United States Patent
Dahlqvist et al.

(10) Patent No.: US 7,427,593 B1
(45) Date of Patent: Sep. 23, 2008

(54) METHODS OF MAKING TRIACYLGLYCEROL USING PHOSPHOLIPID:DIACYLGLYCEROL ACYLTRANSFERASE

(75) Inventors: Andres Dahlqvist, Furulund (SE); Ulf Stahl, Uppsala (SE); Marit Lenman, Lund (SE); Antoni Banas, Siedlce (PL); Hans Ronne, Uppsala (SE); Sten Stymme, Svalöv (SE)

(73) Assignee: BASF Plant Science GmbH, Ludwigshafen (DE)

( * ) Notice: Subject to any disclaimer, the term of this patent is extended or adjusted under 35 U.S.C. 154(b) by 0 days.

(21) Appl. No.: 09/537,710

(22) Filed: Mar. 30, 2000

Related U.S. Application Data

(63) Continuation of application No. 09/329,802, filed on Jun. 10, 1999, now abandoned.

(60) Provisional application No. 60/180,687, filed on Feb. 7, 2000, provisional application No. 60/132,010, filed on Apr. 30, 1999.

(30) Foreign Application Priority Data

Apr. 1, 1999 (EP) .................................. 99106656

(51) Int. Cl.
*A61K 38/00* (2006.01)
(52) U.S. Cl. ............................ 514/12; 514/2; 435/69.1; 435/320.1; 435/252; 435/6; 800/281
(58) Field of Classification Search .................. 435/159
See application file for complete search history.

(56) References Cited

U.S. PATENT DOCUMENTS 6,791,008 B1 * 9/2004 Banas et al. ................. 800/281
7,157,619 B1 * 1/2007 Lassner et al. ............... 800/281
2004/0088759 A1 5/2004 Cahoon et al.

FOREIGN PATENT DOCUMENTS

WO    WO 96/38573    * 12/1996
WO    WO9855631      12/1998

OTHER PUBLICATIONS

Yu et al. Molecular Cloning and Characterization of Two Isoforms of *Saccharomyces cerevisiae* Acyl-CoA:Sterol Acyltransferase. J. Biol. Chem. (1996) 271(39):24157-24163.*
Dahlqvist et al. Phospholipid:diacylglycerol acyltransferase: An enzyme that catalyzes the acyl-CoA-independent formation of triacylglycerol in yeast and plants. PNAS (2000) 97(12):6487-6492.*
Verhasselt et al. Twelve open reading frames revealed in the 23.6 kb segment flanking the centromere on the Saccharomyces cerevisiae chromosome XIV right arm. Yeast (1994) 10(10):1355-1361.*
Sorger et al. Triacylglycerol biosynthesis in yeast. Appl. Microbiol. Biotechnol. (2003) 61:289-299.*
Oelkers et al. A Lecithin Cholesterol Acyltransferase-like Gene Mediates Diacylglycerol Esterification in Yeast. J. Biol. Chem. (2000) 275(21):15609-15612.*
Verhasselt et al., Yeast, vol. 10, No. 10, pp. 1355-1361, 1994.*
McLean et al., *Nucleic Acids Research*, vol. 14, No. 23, 1988, pp. 9397-9406.
Stobart et al., *Planta*, v. 203, 1997, p. 58-66.

* cited by examiner

*Primary Examiner*—Hope A Robinson
(74) *Attorney, Agent, or Firm*—Novak Druce + Quigg LLP

(57) ABSTRACT

The present invention relates to the production of triacylglycerol in a transformed organism or host cell, by means of a nucleotide sequence from *S. cerevisiae*, whereby said enzyme catalyzes the transfer of fatty acids from phospholipids to diacylglycerol in any acyl-CoA-independent reaction. The transformation of the organism or host cell results in increased oil content.

8 Claims, 4 Drawing Sheets

Fig. 1
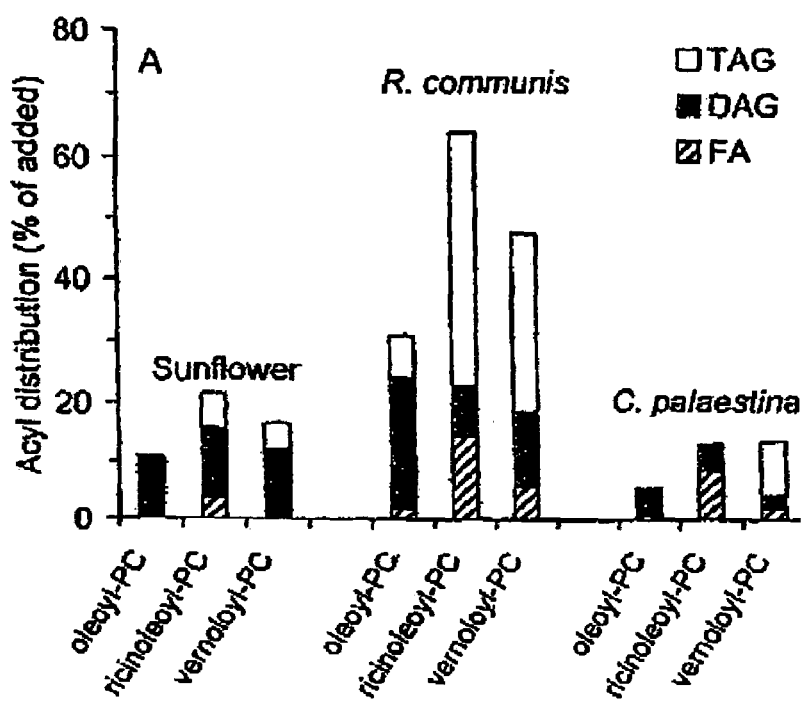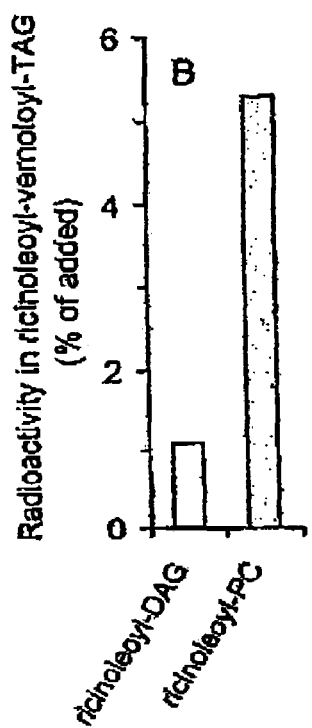
Fig. 1a
Fig. 1b

Fig. 3
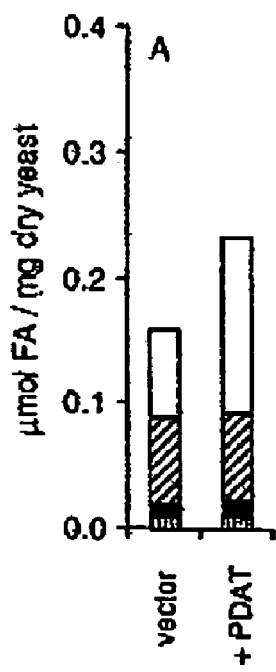
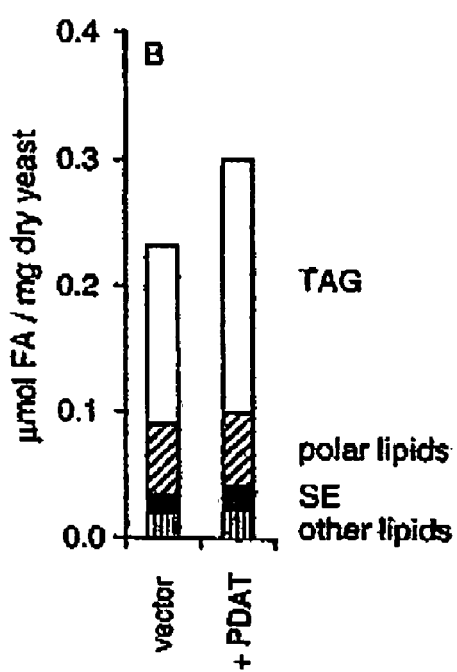
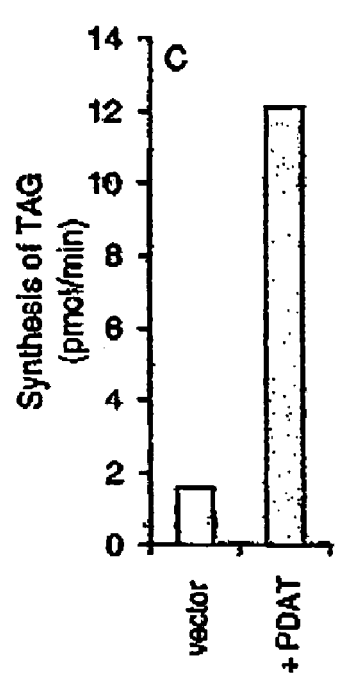
Fig. 3a  Fig. 3b  Fig. 3c

Fig. 4
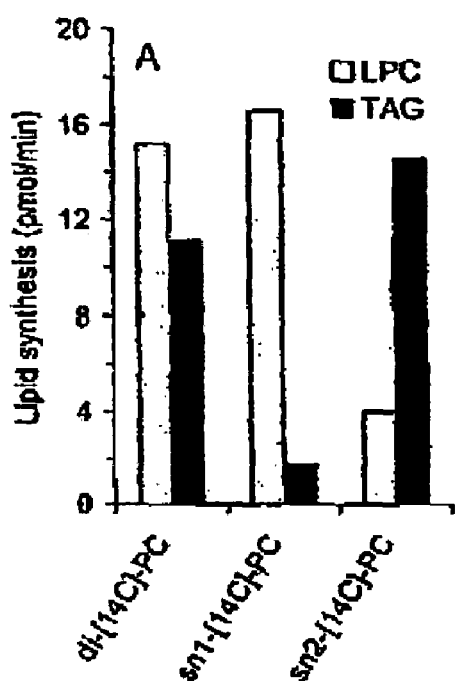
Fig. 4a
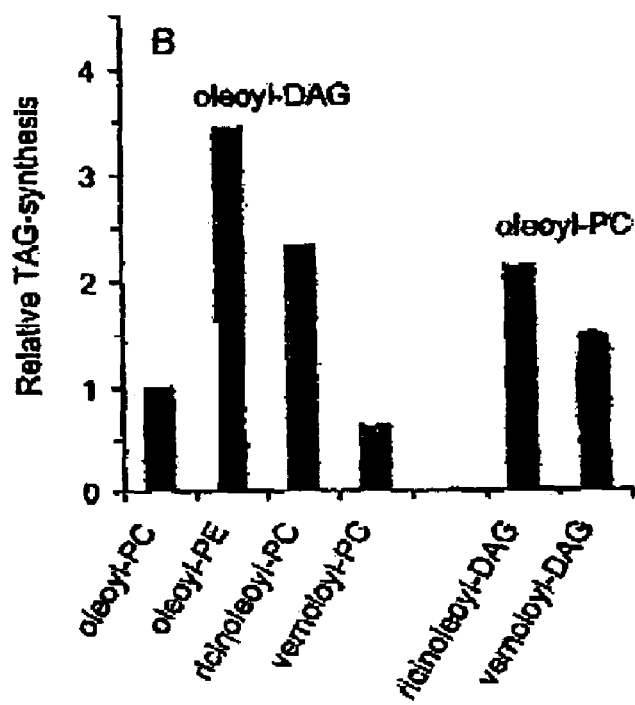
Fig. 4b

SEQUENCE LISTING

```
<160> NUMBER OF SEQ ID NOS: 21

<210> SEQ ID NO 1
<211> LENGTH: 1986
<212> TYPE: DNA
<213> ORGANISM: Saccharomyces cerevisiae
<220> FEATURE:
<221> NAME/KEY: CDS
<222> LOCATION: (1)..(1983)

<400> SEQUENCE: 1
```

```
atg ggc aca ctg ttt cga aga aat gtc cag aac caa aag agt gat tct      48
Met Gly Thr Leu Phe Arg Arg Asn Val Gln Asn Gln Lys Ser Asp Ser
 1               5                  10                  15 gat gaa aac aat aaa ggg ggt tct gtt cat aac aag cga gag agc aga      96
Asp Glu Asn Asn Lys Gly Gly Ser Val His Asn Lys Arg Glu Ser Arg
             20                  25                  30 aac cac att cat cat caa cag gga tta ggc cat aag aga aga agg ggt     144
Asn His Ile His His Gln Gln Gly Leu Gly His Lys Arg Arg Arg Gly
         35                  40                  45 att agt ggc agt gca aaa aga aat gag cgt ggc aaa gat ttc gac agg     192
Ile Ser Gly Ser Ala Lys Arg Asn Glu Arg Gly Lys Asp Phe Asp Arg
 50                  55                  60 aaa aga gac ggg aac ggt aga aaa cgt tgg aga gat tcc aga aga ctg     240
Lys Arg Asp Gly Asn Gly Arg Lys Arg Trp Arg Asp Ser Arg Arg Leu
 65                  70                  75                  80 att ttc att ctt ggt gca ttc tta ggt gta ctt ttg ccg ttt agc ttt     288
Ile Phe Ile Leu Gly Ala Phe Leu Gly Val Leu Leu Pro Phe Ser Phe
                 85                  90                  95 ggc gct tat cat gtt cat aat agc gat agc gac ttg ttt gac aac ttt     336
Gly Ala Tyr His Val His Asn Ser Asp Ser Asp Leu Phe Asp Asn Phe
             100                 105                 110 gta aat ttt gat tca ctt aaa gtg tat ttg gat gat tgg aaa gat gtt     384
Val Asn Phe Asp Ser Leu Lys Val Tyr Leu Asp Asp Trp Lys Asp Val
         115                 120                 125 ctc cca caa ggt ata agt tcg ttt att gat gat att cag gct ggt aac     432
Leu Pro Gln Gly Ile Ser Ser Phe Ile Asp Asp Ile Gln Ala Gly Asn
 130                 135                 140 tac tcc aca tct tct tta gat gat ctc agt gaa aat ttt gcc gtt ggt     480
Tyr Ser Thr Ser Ser Leu Asp Asp Leu Ser Glu Asn Phe Ala Val Gly
145                 150                 155                 160 aaa caa ctc tta cgt gat tat aat atc gag gcc aaa cat cct gtt gta     528
Lys Gln Leu Leu Arg Asp Tyr Asn Ile Glu Ala Lys His Pro Val Val
                 165                 170                 175 atg gtt cct ggt gtc att tct acg gga att gaa agc tgg gga gtt att     576
Met Val Pro Gly Val Ile Ser Thr Gly Ile Glu Ser Trp Gly Val Ile
             180                 185                 190 gga gac gat gag tgc gat agt tct gcg cat ttt cgt aaa cgg ctg tgg     624
Gly Asp Asp Glu Cys Asp Ser Ser Ala His Phe Arg Lys Arg Leu Trp
         195                 200                 205 gga agt ttt tac atg ctg aga aca atg gtt atg gat aaa gtt tgt tgg     672
Gly Ser Phe Tyr Met Leu Arg Thr Met Val Met Asp Lys Val Cys Trp
 210                 215                 220 ttg aaa cat gta atg tta gat cct gaa aca ggt ctg gac cca ccg aac     720
Leu Lys His Val Met Leu Asp Pro Glu Thr Gly Leu Asp Pro Pro Asn
225                 230                 235                 240 ttt acg cta cgt gca gca cag ggc ttc gaa tca act gat tat ttc atc     768
Phe Thr Leu Arg Ala Ala Gln Gly Phe Glu Ser Thr Asp Tyr Phe Ile
                 245                 250                 255 gca ggg tat tgg att tgg aac aaa gtt ttc caa aat ctg gga gta att     816
Ala Gly Tyr Trp Ile Trp Asn Lys Val Phe Gln Asn Leu Gly Val Ile
             260                 265                 270 ggc tat gaa ccc aat aaa atg acg agt gct gcg tat gat tgg agg ctt     864
Gly Tyr Glu Pro Asn Lys Met Thr Ser Ala Ala Tyr Asp Trp Arg Leu
         275                 280                 285 gca tat tta gat cta gaa aga cgc gat agg tac ttt acg aag cta aag     912
Ala Tyr Leu Asp Leu Glu Arg Arg Asp Arg Tyr Phe Thr Lys Leu Lys
 290                 295                 300 gaa caa atc gaa ctg ttt cat caa ttg agt ggt gaa aaa gtt tgt tta     960
Glu Gln Ile Glu Leu Phe His Gln Leu Ser Gly Glu Lys Val Cys Leu
```

-continued

```
        305                 310                 315                 320
att gga cat tct atg ggt tct cag att atc ttt tac ttt atg aaa tgg     1008
Ile Gly His Ser Met Gly Ser Gln Ile Ile Phe Tyr Phe Met Lys Trp
                325                 330                 335 gtc gag gct gaa ggc cct ctt tac ggt aat ggt ggt cgt ggc tgg gtt     1056
Val Glu Ala Glu Gly Pro Leu Tyr Gly Asn Gly Gly Arg Gly Trp Val
            340                 345                 350 aac gaa cac ata gat tca ttc att aat gca gca ggg acg ctt ctg ggc     1104
Asn Glu His Ile Asp Ser Phe Ile Asn Ala Ala Gly Thr Leu Leu Gly
        355                 360                 365 gct cca aag gca gtt cca gct cta att agt ggt gaa atg aaa gat acc     1152
Ala Pro Lys Ala Val Pro Ala Leu Ile Ser Gly Glu Met Lys Asp Thr
    370                 375                 380 att caa tta aat acg tta gcc atg tat ggt ttg gaa aag ttc ttc tca     1200
Ile Gln Leu Asn Thr Leu Ala Met Tyr Gly Leu Glu Lys Phe Phe Ser
385                 390                 395                 400 aga att gag aga gta aaa atg tta caa acg tgg ggt ggt ata cca tca     1248
Arg Ile Glu Arg Val Lys Met Leu Gln Thr Trp Gly Gly Ile Pro Ser
                405                 410                 415 atg cta cca aag gga gaa gag gtc att tgg ggg gat atg aag tca tct     1296
Met Leu Pro Lys Gly Glu Glu Val Ile Trp Gly Asp Met Lys Ser Ser
            420                 425                 430 tca gag gat gca ttg aat aac aac act gac aca tac ggc aat ttc att     1344
Ser Glu Asp Ala Leu Asn Asn Asn Thr Asp Thr Tyr Gly Asn Phe Ile
        435                 440                 445 cga ttt gaa agg aat acg agc gat gct ttc aac aaa aat ttg aca atg     1392
Arg Phe Glu Arg Asn Thr Ser Asp Ala Phe Asn Lys Asn Leu Thr Met
    450                 455                 460 aaa gac gcc att aac atg aca tta tcg ata tca cct gaa tgg ctc caa     1440
Lys Asp Ala Ile Asn Met Thr Leu Ser Ile Ser Pro Glu Trp Leu Gln
465                 470                 475                 480 aga aga gta cat gag cag tac tcg ttc ggc tat tcc aag aat gaa gaa     1488
Arg Arg Val His Glu Gln Tyr Ser Phe Gly Tyr Ser Lys Asn Glu Glu
                485                 490                 495 gag tta aga aaa aat gag cta cac cac aag cac tgg tcg aat cca atg     1536
Glu Leu Arg Lys Asn Glu Leu His His Lys His Trp Ser Asn Pro Met
            500                 505                 510 gaa gta cca ctt cca gaa gct ccc cac atg aaa atc tat tgt ata tac     1584
Glu Val Pro Leu Pro Glu Ala Pro His Met Lys Ile Tyr Cys Ile Tyr
        515                 520                 525 ggg gtg aac aac cca act gaa agg gca tat gta tat aag gaa gag gat     1632
Gly Val Asn Asn Pro Thr Glu Arg Ala Tyr Val Tyr Lys Glu Glu Asp
    530                 535                 540 gac tcc tct gct ctg aat ttg acc atc gac tac gaa agc aag caa cct     1680
Asp Ser Ser Ala Leu Asn Leu Thr Ile Asp Tyr Glu Ser Lys Gln Pro
545                 550                 555                 560 gta ttc ctc acc gag ggg gac gga acc gtt ccg ctc gtg gcg cat tca     1728
Val Phe Leu Thr Glu Gly Asp Gly Thr Val Pro Leu Val Ala His Ser
                565                 570                 575 atg tgt cac aaa tgg gcc cag ggt gct tca ccg tac aac cct gcc gga     1776
Met Cys His Lys Trp Ala Gln Gly Ala Ser Pro Tyr Asn Pro Ala Gly
            580                 585                 590 att aac gtt act att gtg gaa atg aaa cac cag cca gat cga ttt gat     1824
Ile Asn Val Thr Ile Val Glu Met Lys His Gln Pro Asp Arg Phe Asp
        595                 600                 605 ata cgt ggt gga gca aaa agc gcc gaa cac gta gac atc ctc ggc agc     1872
Ile Arg Gly Gly Ala Lys Ser Ala Glu His Val Asp Ile Leu Gly Ser
    610                 615                 620 gcg gag ttg aac gat tac atc ttg aaa att gca agc ggt aat ggc gat     1920
Ala Glu Leu Asn Asp Tyr Ile Leu Lys Ile Ala Ser Gly Asn Gly Asp
```

```
Ala Glu Leu Asn Asp Tyr Ile Leu Lys Ile Ala Ser Gly Asn Gly Asp
625                 630                 635                 640 ctc gtc gag cca cgc caa ttg tct aat ttg agc cag tgg gtt tct cag        1968
Leu Val Glu Pro Arg Gln Leu Ser Asn Leu Ser Gln Trp Val Ser Gln
                645                 650                 655 atg ccc ttc cca atg taa                                                1986
Met Pro Phe Pro Met
            660

<210> SEQ ID NO 2
<211> LENGTH: 661
<212> TYPE: PRT
<213> ORGANISM: Saccharomyces cerevisiae

<400> SEQUENCE: 2

Met Gly Thr Leu Phe Arg Arg Asn Val Gln Asn Gln Lys Ser Asp Ser
 1               5                  10                  15

Asp Glu Asn Asn Lys Gly Gly Ser Val His Asn Lys Arg Glu Ser Arg
                20                  25                  30

Asn His Ile His His Gln Gln Gly Leu Gly His Lys Arg Arg Arg Gly
            35                  40                  45

Ile Ser Gly Ser Ala Lys Arg Asn Glu Arg Gly Lys Asp Phe Asp Arg
        50                  55                  60

Lys Arg Asp Gly Asn Gly Arg Lys Arg Trp Arg Asp Ser Arg Arg Leu
65                  70                  75                  80

Ile Phe Ile Leu Gly Ala Phe Leu Gly Val Leu Pro Phe Ser Phe
                85                  90                  95

Gly Ala Tyr His Val His Asn Ser Asp Ser Asp Leu Phe Asp Asn Phe
            100                 105                 110

Val Asn Phe Asp Ser Leu Lys Val Tyr Leu Asp Asp Trp Lys Asp Val
        115                 120                 125

Leu Pro Gln Gly Ile Ser Ser Phe Ile Asp Asp Ile Gln Ala Gly Asn
    130                 135                 140

Tyr Ser Thr Ser Ser Leu Asp Asp Leu Ser Glu Asn Phe Ala Val Gly
145                 150                 155                 160

Lys Gln Leu Leu Arg Asp Tyr Asn Ile Glu Ala Lys His Pro Val Val
                165                 170                 175

Met Val Pro Gly Val Ile Ser Thr Gly Ile Glu Ser Trp Gly Val Ile
            180                 185                 190

Gly Asp Asp Glu Cys Asp Ser Ser Ala His Phe Arg Lys Arg Leu Trp
        195                 200                 205

Gly Ser Phe Tyr Met Leu Arg Thr Met Val Met Asp Lys Val Cys Trp
    210                 215                 220

Leu Lys His Val Met Leu Asp Pro Glu Thr Gly Leu Asp Pro Pro Asn
225                 230                 235                 240

Phe Thr Leu Arg Ala Ala Gln Gly Phe Glu Ser Thr Asp Tyr Phe Ile
                245                 250                 255

Ala Gly Tyr Trp Ile Trp Asn Lys Val Phe Gln Asn Leu Gly Val Ile
            260                 265                 270

Gly Tyr Glu Pro Asn Lys Met Thr Ser Ala Ala Tyr Asp Trp Arg Leu
        275                 280                 285

Ala Tyr Leu Asp Leu Glu Arg Arg Asp Arg Tyr Phe Thr Lys Leu Lys
    290                 295                 300

Glu Gln Ile Glu Leu Phe His Gln Leu Ser Gly Glu Lys Val Cys Leu
305                 310                 315                 320
```

| | | | | | | | | | | | |
|---|---|---|---|---|---|---|---|---|---|---|---|
|Ile|Gly|His|Ser|Met|Gly|Ser|Gln|Ile|Ile|Phe|Tyr|Phe|Met|Lys|Trp|

Ile Gly His Ser Met Gly Ser Gln Ile Ile Phe Tyr Phe Met Lys Trp
                325                 330                 335

Val Glu Ala Glu Gly Pro Leu Tyr Gly Asn Gly Arg Gly Trp Val
                340                 345             350

Asn Glu His Ile Asp Ser Phe Ile Asn Ala Ala Gly Thr Leu Leu Gly
                355                 360                 365

Ala Pro Lys Ala Val Pro Ala Leu Ile Ser Gly Glu Met Lys Asp Thr
370                 375                 380

Ile Gln Leu Asn Thr Leu Ala Met Tyr Gly Leu Glu Lys Phe Phe Ser
385                 390                 395                 400

Arg Ile Glu Arg Val Lys Met Leu Gln Thr Trp Gly Ile Pro Ser
                405                 410                 415

Met Leu Pro Lys Gly Glu Val Ile Trp Gly Asp Met Lys Ser Ser
                420                 425                 430

Ser Glu Asp Ala Leu Asn Asn Asn Thr Asp Thr Tyr Gly Asn Phe Ile
                435                 440                 445

Arg Phe Glu Arg Asn Thr Ser Asp Ala Phe Asn Lys Asn Leu Thr Met
                450                 455                 460

Lys Asp Ala Ile Asn Met Thr Leu Ser Ile Ser Pro Glu Trp Leu Gln
465                 470                 475                 480

Arg Arg Val His Glu Gln Tyr Ser Phe Gly Tyr Ser Lys Asn Glu Glu
                485                 490                 495

Glu Leu Arg Lys Asn Glu Leu His His Lys His Trp Ser Asn Pro Met
                500                 505                 510

Glu Val Pro Leu Pro Glu Ala Pro His Met Lys Ile Tyr Cys Ile Tyr
                515                 520                 525

Gly Val Asn Asn Pro Thr Glu Arg Ala Tyr Val Tyr Lys Glu Asp
                530                 535                 540

Asp Ser Ser Ala Leu Asn Leu Thr Ile Asp Tyr Glu Ser Lys Gln Pro
545                 550                 555                 560

Val Phe Leu Thr Glu Gly Asp Gly Thr Val Pro Leu Val Ala His Ser
                565                 570                 575

Met Cys His Lys Trp Ala Gln Gly Ala Ser Pro Tyr Asn Pro Ala Gly
                580                 585                 590

Ile Asn Val Thr Ile Val Glu Met Lys His Gln Pro Asp Arg Phe Asp
                595                 600                 605

Ile Arg Gly Gly Ala Lys Ser Ala Glu His Val Asp Ile Leu Gly Ser
                610                 615                 620

Ala Glu Leu Asn Asp Tyr Ile Leu Lys Ile Ala Ser Gly Asn Gly Asp
625                 630                 635                 640

Leu Val Glu Pro Arg Gln Leu Ser Asn Leu Ser Gln Trp Val Ser Gln
                645                 650                 655

Met Pro Phe Pro Met
            660

<210> SEQ ID NO 3
<211> LENGTH: 2312
<212> TYPE: DNA
<213> ORGANISM: Schizosaccharomyces pombe

<400> SEQUENCE: 3
atggcgtctt ccaagaagag caaaactcat aagaaaaaga aagaagtcaa atctcctatc    60
gacttaccaa attcaaagaa accaactcgc gctttgagtg agcaaccttc agcgtccgaa   120
acacaatctg tttcaaataa atcaagaaaa tctaaatttg gaaaaagatt gaattttata   180

```
ttgggcgcta ttttgggaat atgcggtgct ttttttttcg ctgttggaga cgacaatgct      240
gttttcgacc ctgctacgtt agataaattt gggaatatgc taggctcttc agacttgttt      300
gatgacatta aaggatattt atcttataat gtgtttaagg atgcacccttt tactacggac     360 aagccttcgc agtctcctag cggaaatgaa gttcaagttg gtcttgatat gtacaatgag      420
ggatatcgaa gtgaccatcc tgttattatg gttcctggtg ttatcagctc aggattagaa      480
agttggtcgt ttaataattg ctcgattcct tactttagga aacgtctttg gggtagctgg      540
tctatgctga aggcaatgtt ccttgacaag caatgctggc ttgaacattt aatgcttgat      600
aaaaaaaccg gcttggatcc gaagggaatt aagctgcgag cagctcaggg gtttgaagca      660
gctgattttt ttatcacggg ctattggatt tggagtaaag taattgaaaa ccttgctgca      720
attggttatg agcctaataa catgttaagt gcttcttacg attggcggtt atcatatgca      780
aatttagagg aacgtgataa atattttttca aagttaaaaa tgttcattga gtacagcaac      840
attgtacata agaaaaaggt agtgttgatt tctcactcca tgggttcaca ggttacgtac      900 tatttttta agtgggttga agctgagggc tacggaaatg gtggaccgac ttgggttaat      960
gatcatattg aagcatttat aaatgtgagt ctcgatggtt gtttgactac gtttctaact      1020
tttgaataga tatcgggatc tttgattgga gcacccaaaa cagtggcagc gcttttatcg     1080
ggtgaaatga aagatacagg tattgtaatt acattaaaca tgttaatatt taattttttgc    1140 taaccgtttt aagctcaatt gaatcagttt tcggtctatg ggtaagcaat aaattgttga     1200
gatttgttac taatttactg tttagttttgg aaaaattttt ttcccgttct gaggtatatt    1260
caaaaataca aatgtgctct acttttttcta acttttaata gagagccatg atggttcgca    1320
ctatgggagg agttagttct atgcttccta aaggaggcga tgttgtatgg ggaaatgcca     1380
gttgggtaag aaatatgtgc tgttaatttt ttattaatat ttaggctcca gatgatctta     1440
atcaaacaaa ttttttccaat ggtgcaatta ttcgatatag agaagacatt gataaggacc    1500
acgatgaatt tgacatagat gatgcattac aattttttaaa aaatgttaca gatgacgatt    1560
ttaaagtcat gctagcgaaa aattattccc acggtcttgc ttggactgaa aaagaagtgt     1620
taaaaaataa cgaaatgccg tctaaatgga taaatccgct agaagtaaga acattaaagt     1680
tactaaatta tactaaccca aatagactag tcttccttat gctcctgata tgaaaattta     1740
ttgcgttcac ggggtcggaa aaccaactga gagaggttat tattatacta ataatcctga    1800
ggggcaacct gtcattgatt cctcggttaa tgatggaaca aaagttgaaa atgtgagaga    1860
atttatgttt caaacattct attaactgtt ttattagggt attgttatgg atgatggtga    1920 tggaactta ccaatattag ccccttggttt ggtgtgcaat aaagtttggc aaacaaaaag    1980
gtttaatcct gctaatacaa gtatcacaaa ttatgaaatc aagcatgaac ctgctgcgtt    2040
tgatctgaga ggaggacctc gctcggcaga acacgtcgat atacttggac attcagagct     2100
aaatgtatgt tcattttacc ttacaaattt ctattactaa ctcttgaaat aaggaaatta    2160
ttttaaaagt ttcatcaggc catggtgact cggtaccaaa ccgttatata tcagatatcc     2220
agtacggaca taagttttgt agattgcaat taactaacta accgaacagg gaaataataa    2280
atgagataaa tctcgataaa cctagaaatt aa                                    2312
```

<210> SEQ ID NO 4
<211> LENGTH: 3685
<212> TYPE: DNA
<213> ORGANISM: Arabidopsis thaliana

```
<400> SEQUENCE: 4 atgccccctta ttcatcggaa aaagccgacg gagaaaccat cgacgccgcc atctgaagag    60
gtggtgcacg atgaggattc gcaaaagaaa ccacacgaat cttccaaatc ccaccataag   120
aaatcgaacg gaggagggaa gtggtcgtgc atcgattctt gttgttggtt cattgggtgt   180
gtgtgtgtaa cctggtggtt tcttctcttc ctttacaacg caatgcctgc gagcttccct   240
cagtatgtaa cggagcgaat cacgggtcct ttgcctgacc cgcccggtgt taagctcaaa   300
aaagaaggtc ttaaggcgaa acatcctgtt gtcttcattc ctgggattgt caccggtggg   360
ctcgagcttt gggaaggcaa acaatgcgct gatggtttat ttagaaaacg tttgtggggt   420
ggaactttg gtgaagtcta caaaggtga gctcaacaat tctcactctt cctttatatt   480
gggatttgga ttggatctga tgagatcacg cacttgttgc ttcttcaaca tcactcaaac   540
tttaattcca tgtttgtctg tcttactctt tactttttt tttttttgat gtgaaacgct   600
attttcttaa gagactattt ctgtatgtgt aaggtaagcg ttccaaggac gtaattggct   660
tggactattt ctgtttgatt gttaacttta ggatataaaa tagctgcctt ggaatttcaa   720
gtcatcttat tgccaaatct gttgctagac atgccctaga gtccgttcat aacaagttac   780
ttcctttact gtcgttgcgt gtagatttag ctttgtgtag cgtataatga agtagtgttt   840
tatgttttgt tgggaataga gaagttctaa ctacatctgt ggaaagtgtg ttcaggctgt   900
gatagaggac tgttgcttta ttattcaact atgtatatgt gtaattaaag ctagttcctt   960
tttgatcttt cagctcaatg tgcttttctc aattttttc tcaatttcaa agtttcacat  1020
cgagtttatt cacatgtctt gaatttcgtc catcctcgtt ctgttatcca gctttgaact  1080
cctcccgacc ctgctatgga tatattaaaa aaaaagtgtt ttgtggggttg catctttgtt  1140
acgatctgca tcttcttctt tcggctcagt gttcatgttt ttgctatggt agagatgggc  1200
aatgttattg ttgatggtaa cagtggtata gttgatagta tcttaactaa tcaattatct  1260
cttgattca ggcctctatg ttgggtggaa cacatgtcac ttgacaatga aactgggttg  1320
gatccagctg gtattagagt tcgagctgta tcaggactcg tggctgctga ctactttgct  1380
cctggctact ttgtctgggc agtgctgatt gctaaccttg cacatattgg atatgaagag  1440
aaaaatatgt acatggctgc atatgactgg cggctttcgt ttcagaacac agaggttctt  1500
ttctcatcgt tctttctatt attctgttcc atgttacgtt tctttcttca ttacttaagg  1560
cttaaatatg tttcatgttg aattaatagg tacgtgatca gactcttagc cgtatgaaaa  1620
gtaatataga gttgatggtt tctaccaacg gtggaaaaaa agcagttata gttccgcatt  1680
ccatggggtg cttgtatttt ctacatttta tgaagtgggt tgaggcacca gctcctctgg  1740
gtggcggggg tgggccagat tggtgtgcaa agtatattaa ggcggtgatg aacattggtg  1800
gaccatttct tggtgttcca aaagctgttg cagggctttt ctctgctgaa gcaaaggatg  1860
ttgcagttgc caggtattga atatctgctt atactttga tgatcagaac cttggctctg  1920
gaactcaaag ttattctact aaatatcaat tctaataaca ttgctatatt atcgctgcaa  1980
ctgacattgg ttgattattt ttgctgctta tgtaactgaa actctcttga gattagacaa  2040
atgatgaatt gataattctt acgcattgct ctgtgatgac cagtttctta gcttcgacga  2100
taacatttgt catactgtct tttggagggc attgaatttt gctatggaaa gcgctggagc  2160
ttccatgctt gcattcttta ccaattagcg ttattctgct tctttcaatt ttcttgtata  2220
tgcatctatg gtctttatt tcttcttaat taaagactcg ttggattagt tgctctatta  2280
gtcacttggt tccttaatat agaactttac tttcttcgaa aattgcagag cgattgcccc  2340
```

-continued

```
aggattctta gacaccgata tatttagact tcagaccttg cagcatgtaa tgagaatgac    2400
acgcacatgg gactcaacaa tgtctatgtt accgaaggga ggtgacacga tatggggcgg    2460
gcttgattgg tcaccggaga aaggccacac ctgttgtggg aaaaagcaaa agaacaacga    2520
aacttgtggt gaagcaggtg aaaacggagt ttccaagaaa agtcctgtta actatggaag    2580
gatgatatct tttgggaaag aagtagcaga ggctgcgcca tctgagatta ataatattga    2640
ttttcgagta aggacatata atcataata aaccttgtac attttgtgat tgtatgatga    2700
atatctgtac atttatctg gtgaaggggtg ctgtcaaagg tcagagtatc ccaaatcaca    2760
cctgtcgtga cgtgtggaca gagtaccatg acatgggaat tgctgggatc aaagctatcg    2820
ctgagtataa ggtctacact gctggtgaag ctatagatct actacattat gttgctccta    2880
agatgatggc gcgtggtgcc gctcatttct cttatggaat tgctgatgat ttggatgaca    2940
ccaagtatca agatcccaaa tactggtcaa atccgttaga gacaaagtaa gtgatttctt    3000
gattccaact gtatccttcg tcctgatgca ttatcagtct ttttgttttc ggtcttgttg    3060
gatatggttt tcagctcaaa gcttacaaag ctgtttctga gcctttctca aaaaggcttg    3120
ctcagtaata ttgaggtgct aaagttgata catgtgactc ttgcttataa atcctccgtt    3180
tggtttgttc tgcttttca gattaccgaa tgctcctgag atggaaatct actcattata    3240
cggagtgggg ataccaacgg aacgagcata cgtatacaag cttaaccagt ctcccgacag    3300
ttgcatcccc tttcagatat tcacttctgc tcacgaggag gacgaagata gctgtctgaa    3360
agcaggagtt tacaatgtgg atggggatga acagtaccc gtcctaagtg ccgggtacat    3420
gtgtgcaaaa gcgtggcgtg gcaagacaag attcaaccct tccggaatca agacttatat    3480
aagagaatac aatcactctc cgccggctaa cctgttggaa gggcgcggga cgcagagtgg    3540
tgcccatgtt gatatcatgg gaaactttgc tttgatcgaa gatatcatga gggttgccgc    3600
cggaggtaac gggtctgata taggacatga ccaggtccac tctggcatat ttgaatggtc    3660
ggagcgtatt gacctgaagc tgtga                                         3685
```

<210> SEQ ID NO 5
<211> LENGTH: 2427
<212> TYPE: DNA
<213> ORGANISM: Arabidopsis thaliana
<220> FEATURE:
<221> NAME/KEY: unsure
<222> LOCATION: 1...2427
<223> OTHER INFORMATION: n= a or g or c or t/u

<400> SEQUENCE: 5

```
agaaacagct ctttgtctct ctcgactgat ctaacaatcc ctaatctgtg ttctaaattc     60
ctggacgaga tttgacaaag tccgtatagc ttaacctggt ttaatttcaa gtgacagata    120
tgccccttat tcatcggaaa aagccgacgg agaaaccatc gacgccgcca tctgaagagg    180
tggtgcacga tgaggattcg caaaagaaac cacacgaatc ttccaaatcc caccataaga    240
aatcgaacgg aggagggaag tggtcgtgca tcgattcttg ttgttggttc attgggtgtg    300
tgtgtgtaac ctggtggttt cttctcttcc tttacaacgc aatgcctgcg agcttccctc    360
agtatgtaac ggagcgaatc acgggtcctt tgcctgaccc gccggtgtt aagctcaaaa    420 aaagaaggtc ttaaggcgaa acatcctgtt gtcttcattc ctgggattgt caccggtggg    480
ctcgagcttt ggaaggcaa acaatgcgct gatggtttat ttagaaaacg tttgtggggt    540
ggaacttttg gtgaagtcta caaaaggcct ctatgttggg tggaacacat gtcacttgac    600
```

```
aatgaaactg ggttggatcc agctggtatt agagttcgag ctgtatcagg actcgtggct     660
gctgactact ttgctcctgg ctactttgtc tgggcagtgc tgattgctaa ccttgcacat     720
attggatatg aagagaaaaa tatgtacatg gctgcatatg actggcggct ttcgtttcag     780
aacacagagg tacgtgatca gactcttagc cgtatgaaaa gtaatataga gttgatggtt     840
tctaccaacg gtggaaaaaa agcagttata gttccgcatt ccatggggt cttgtatttt      900 ctacatttta tgaagtgggt tgaggcacca gctcctctgg gtggcggggg tgggccagat     960
tggtgtgcaa agtatattaa ggcggtgatg aacattggtg gaccatttct ggtgttcca    1020 aaagctgttg cagggctttt ctctgctgaa gcaaaggatt tgcagttgc cagagcgatt    1080 gccccaggat tcttagacac cgatatattt agacttcaga ccttgcagca tgtaatgaga    1140 atgcacgca catgggactc aacaatgtct atgttaccga agggaggtga cacgatatgg     1200
ggcgggcttg attggtcacc ggagaaaggc cacacctgtt gtgggaaaaa gcaaagaac     1260 aacgaaactt gtggtgaagc aggtgaaaac ggagtttcca agaaaagtcc tgttaactat    1320
ggaaggatga tatcttttgg gaaagaagta gcagaggctg cgccatctga gattaataat    1380
attgattttc gaggtgctgt caaaggtcag agtatcccaa atcacacctg tcgtgacgtg    1440
tggacagagt accatgacat gggaattgct gggatcaaag ctatcgctga gtataaggtc    1500
tacactgctg gtgaagctat agatctacta cattatgttg ctcctaagat gatggcgcgt    1560
ggtgccgctc atttctctta tggaattgct gatgatttgg atgacaccaa gtatcaagat    1620
cccaaatact ggtcaaatcc gttagagaca aaattaccga atgctcctga gatggaaatc    1680
tactcattat acggagtggg gataccaacg gaacgagcat acgtatacaa gcttaaccag    1740
tctcccgaca gttgcatccc cttcagata ttcacttctg ctcacgagga ggacgaagat     1800
agctgtctga aagcaggagt ttacaatgtg gatggggatg aaacagtacc cgtcctaagt    1860
gccgggtaca tgtgtgcaaa agcgtggcgt ggcaagacaa gattcaaccc ttccggaatc    1920
aagacttata taagagaata caatcactct ccgccggcta acctgttgga agggcgcggg    1980
acgcagagtg gtgcccatgt tgatatcatg ggaaactttg ctttgatcga agatatcatg    2040
agggttgccg ccggaggtaa cgggtctgat ataggacatg accaggtcca ctctggcata    2100
tttgaatggt cggagcgtat tgacctgaag ctgtgaatat catgatctct ttaagctgtc    2160
ctgtcagctt atgtgaatcc aatactttga aagagagatc atcatcaatt catcatcatc    2220
gtcatcatca tgatgctcaa ctcacaaaga agcctgagaa tgatactttg gtgcgaaatt    2280 ctcaataccct ctttaatatt cttattgaat gtaaattata caatcctatc taatgtttga   2340
acgataacac aaaacttgct gcngccatgt ttgtttgtct tgtcaaaagc atcaatttgt    2400
gggttaaaaa aaaaaaaaaa aaaaaaa                                         2427
```

<210> SEQ ID NO 6
<211> LENGTH: 671
<212> TYPE: PRT
<213> ORGANISM: Arabidopsis thaliana

<400> SEQUENCE: 6

Met Pro Leu Ile His Arg Lys Lys Pro Thr Glu Lys Pro Ser Thr Pro
1               5                   10                  15

Pro Ser Glu Glu Val Val His Asp Glu Asp Ser Gln Lys Lys Pro His
            20                  25                  30

Glu Ser Ser Lys Ser His His Lys Lys Ser Asn Gly Gly Gly Lys Trp
        35                  40                  45

-continued

```
Ser Cys Ile Asp Ser Cys Cys Trp Phe Ile Gly Cys Val Cys Val Thr
    50              55                  60
Trp Trp Phe Leu Leu Phe Leu Tyr Asn Ala Met Pro Ala Ser Phe Pro
65              70                  75                  80
Gln Tyr Val Thr Glu Arg Ile Thr Gly Pro Leu Pro Asp Pro Pro Gly
                85                  90                  95
Val Lys Leu Lys Lys Glu Gly Leu Lys Ala Lys His Pro Val Val Phe
            100                 105                 110
Ile Pro Gly Ile Val Thr Gly Gly Leu Glu Leu Trp Glu Gly Lys Gln
            115                 120                 125
Cys Ala Asp Gly Leu Phe Arg Lys Arg Leu Trp Gly Gly Thr Phe Gly
    130                 135                 140
Glu Val Tyr Lys Arg Pro Leu Cys Trp Val Glu His Met Ser Leu Asp
145                 150                 155                 160
Asn Glu Thr Gly Leu Asp Pro Ala Gly Ile Arg Val Arg Ala Val Ser
                165                 170                 175
Gly Leu Val Ala Ala Asp Tyr Phe Ala Pro Gly Tyr Phe Val Trp Ala
            180                 185                 190
Val Leu Ile Ala Asn Leu Ala His Ile Gly Tyr Glu Glu Lys Asn Met
            195                 200                 205
Tyr Met Ala Ala Tyr Asp Trp Arg Leu Ser Phe Gln Asn Thr Glu Val
    210                 215                 220
Arg Asp Gln Thr Leu Ser Arg Met Lys Ser Asn Ile Glu Leu Met Val
225                 230                 235                 240
Ser Thr Asn Gly Gly Lys Lys Ala Val Ile Val Pro His Ser Met Gly
                245                 250                 255
Val Leu Tyr Phe Leu His Phe Met Lys Trp Val Glu Ala Pro Ala Pro
            260                 265                 270
Leu Gly Gly Gly Gly Pro Asp Trp Cys Ala Lys Tyr Ile Lys Ala
            275                 280                 285
Val Met Asn Ile Gly Gly Pro Phe Leu Gly Val Pro Lys Ala Val Ala
    290                 295                 300
Gly Leu Phe Ser Ala Glu Ala Lys Asp Val Ala Val Ala Arg Ala Ile
305                 310                 315                 320
Ala Pro Gly Phe Leu Asp Thr Asp Ile Phe Arg Leu Gln Thr Leu Gln
                325                 330                 335
His Val Met Arg Met Thr Arg Thr Trp Asp Ser Thr Met Ser Met Leu
            340                 345                 350
Pro Lys Gly Gly Asp Thr Ile Trp Gly Gly Leu Asp Trp Ser Pro Glu
    355                 360                 365
Lys Gly His Thr Cys Cys Gly Lys Lys Gln Lys Asn Asn Glu Thr Cys
    370                 375                 380
Gly Glu Ala Gly Glu Asn Gly Val Ser Lys Lys Ser Pro Val Asn Tyr
385                 390                 395                 400
Gly Arg Met Ile Ser Phe Gly Lys Glu Val Ala Glu Ala Ala Pro Ser
                405                 410                 415
Glu Ile Asn Asn Ile Asp Phe Arg Gly Ala Val Lys Gly Gln Ser Ile
            420                 425                 430
Pro Asn His Thr Cys Arg Asp Val Trp Thr Glu Tyr His Asp Met Gly
            435                 440                 445
Ile Ala Gly Ile Lys Ala Ile Ala Glu Tyr Lys Val Tyr Thr Ala Gly
    450                 455                 460
Glu Ala Ile Asp Leu Leu His Tyr Val Ala Pro Lys Met Met Ala Arg
```

```
                465                 470                 475                 480
Gly Ala Ala His Phe Ser Tyr Gly Ile Ala Asp Asp Leu Asp Asp Thr
                    485                 490                 495

Lys Tyr Gln Asp Pro Lys Tyr Trp Ser Asn Pro Leu Glu Thr Lys Leu
            500                 505                 510

Pro Asn Ala Pro Glu Met Glu Ile Tyr Ser Leu Tyr Gly Val Gly Ile
        515                 520                 525

Pro Thr Glu Arg Ala Tyr Val Tyr Lys Leu Asn Gln Ser Pro Asp Ser
    530                 535                 540

Cys Ile Pro Phe Gln Ile Phe Thr Ser Ala His Glu Glu Asp Glu Asp
545                 550                 555                 560

Ser Cys Leu Lys Ala Gly Val Tyr Asn Val Asp Gly Asp Glu Thr Val
                565                 570                 575

Pro Val Leu Ser Ala Gly Tyr Met Cys Ala Lys Ala Trp Arg Gly Lys
            580                 585                 590

Thr Arg Phe Asn Pro Ser Gly Ile Lys Thr Tyr Ile Arg Glu Tyr Asn
        595                 600                 605

His Ser Pro Pro Ala Asn Leu Leu Glu Gly Arg Gly Thr Gln Ser Gly
    610                 615                 620

Ala His Val Asp Ile Met Gly Asn Phe Ala Leu Ile Glu Asp Ile Met
625                 630                 635                 640

Arg Val Ala Ala Gly Gly Asn Gly Ser Asp Ile Gly His Asp Gln Val
                645                 650                 655

His Ser Gly Ile Phe Glu Trp Ser Glu Arg Ile Asp Leu Lys Leu
            660                 665                 670

<210> SEQ ID NO 7
<211> LENGTH: 643
<212> TYPE: DNA
<213> ORGANISM: Zea mays
<220> FEATURE:
<221> NAME/KEY: CDS
<222> LOCATION: (1)..(402)
<220> FEATURE:
<221> NAME/KEY: Unsure
<222> LOCATION: 1..643
<223> OTHER INFORMATION: n= a or g or c or t/u
<220> FEATURE:
<221> NAME/KEY: Unsure
<222> LOCATION: 1...643
<223> OTHER INFORMATION: Xaa = unknown

<400> SEQUENCE: 7 cgg gag aaa ata gct gct ttg aag ggg ggt gtt tac tta gcc gat ggt      48
Arg Glu Lys Ile Ala Ala Leu Lys Gly Gly Val Tyr Leu Ala Asp Gly
  1               5                  10                  15 gat gaa act gtt cca gtt ctt agt gcg ggc tac atg tgt gcg aaa gga      96
Asp Glu Thr Val Pro Val Leu Ser Ala Gly Tyr Met Cys Ala Lys Gly
             20                  25                  30 tgg cgt ggc aaa act cgt ttc agc cct gcc ggc agc aag act tac gtg     144
Trp Arg Gly Lys Thr Arg Phe Ser Pro Ala Gly Ser Lys Thr Tyr Val
         35                  40                  45 aga gaa tac agc cat tcg cca ccc tct act ctc ctg gaa ggc agg ggc     192
Arg Glu Tyr Ser His Ser Pro Pro Ser Thr Leu Leu Glu Gly Arg Gly
     50                  55                  60 acc cag agc ggt gca cat gtt gat ata atg ggg aac ttt gct cta att     240
Thr Gln Ser Gly Ala His Val Asp Ile Met Gly Asn Phe Ala Leu Ile
 65                  70                  75                  80 gag gac gtc atc aga ata gct gct ggg gca acc ggt gag gaa att ggt     288
Glu Asp Val Ile Arg Ile Ala Ala Gly Ala Thr Gly Glu Glu Ile Gly
```

```
                    85              90                  95
ggc gat cag gtt tat tca gat ata ttc aag tgg tca gag aaa atc aaa    336
Gly Asp Gln Val Tyr Ser Asp Ile Phe Lys Trp Ser Glu Lys Ile Lys
            100                 105                 110 ttg aaa ttg taa cct atg gga agt taa aga agt gcc gac ccg ttt att    384
Leu Lys Leu Xaa Pro Met Gly Ser Xaa Arg Ser Ala Asp Pro Phe Ile
            115                 120                 125 gcg ttc caa agt gtc ctg cctgagtgca actctggatt ttgcttaaat           432
Ala Phe Gln Ser Val Leu
            130 attgtaattt ttcacgcttc attcgtccct ttgtcaaatt tacatttgac aggacgccaa  492 tgcgatacga tgttgtaccg ctattttcag cattgtatat taaactgtac aggtgtaagt  552 tgcatttgcc agctgaaatt gtgtagtcgt tttctttacg atttaatanc aagtggcgga  612 gcagtgcccc aagcnaaaaa aaaaaaaaaa a                                 643

<210> SEQ ID NO 8
<211> LENGTH: 115
<212> TYPE: PRT
<213> ORGANISM: Zea mays

<400> SEQUENCE: 8

Arg Glu Lys Ile Ala Ala Leu Lys Gly Gly Val Tyr Leu Ala Asp Gly
 1               5                  10                  15

Asp Glu Thr Val Pro Val Leu Ser Ala Gly Tyr Met Cys Ala Lys Gly
            20                  25                  30

Trp Arg Gly Lys Thr Arg Phe Ser Pro Ala Gly Ser Lys Thr Tyr Val
        35                  40                  45

Arg Glu Tyr Ser His Ser Pro Pro Ser Thr Leu Leu Glu Gly Arg Gly
    50                  55                  60

Thr Gln Ser Gly Ala His Val Asp Ile Met Gly Asn Phe Ala Leu Ile
65                  70                  75                  80

Glu Asp Val Ile Arg Ile Ala Ala Gly Ala Thr Gly Glu Glu Ile Gly
                85                  90                  95

Gly Asp Gln Val Tyr Ser Asp Ile Phe Lys Trp Ser Glu Lys Ile Lys
            100                 105                 110

Leu Lys Leu
        115

<210> SEQ ID NO 9
<211> LENGTH: 616
<212> TYPE: DNA
<213> ORGANISM: Neurospora crassa
<220> FEATURE:
<221> NAME/KEY: Unsure
<222> LOCATION: 1..616
<223> OTHER INFORMATION: n= a or g or c or t/u

<400> SEQUENCE: 9
ggtggcgaag acganggcgg aagttggagg ctaacgagaa tgacnctcgg agatggatct   60
accctctaga gacacgacta ccnttgcacc cagcctcaag gtntacngtt tntatgggta  120
ggaagccgac ggagcgagcc tacatctatc tggcgcccga tcccgggacg acaacgcatc  180
tttagatgac gatcgatacg actttgactn aggggcacat tgaccacggt gtgattttgg  240
gcgaaggcga tggcacagtg aaccttatga gtttgggta cctgtgcaat aagggtgga   300 aaatgaagag atacaatcct gcgggctcaa aaataaccgt ggtcgagatg ccgcatgaac  360
cagaacggtt caatccgaga ggagggccga atacggcgga tcacgtggat attctaggaa  420
```

```
ggcagaatct aaacgagtac attcttaaag tggcggcagg tcgaggcgat acaattgagg      480
attttattac tagtaatatt cttaaatatg tagaaaaggt tgaaatttat gaagagtaat      540
taaatacggc acataggtta ctcaatagta tgactaatta aaaaaaaatt ttttttctaa      600
aaaaaaaaaa aaaaaa                                                     616

<210> SEQ ID NO 10
<211> LENGTH: 1562
<212> TYPE: DNA
<213> ORGANISM: Arabidopsis thaliana

<400> SEQUENCE: 10
atgaaaaaaa tatcttcaca ttattcggta gtcatagcga tactcgttgt ggtgacgatg       60
acctcgatgt gtcaagctgt gggtagcaac gtgtacccct tgattctggt tccaggaaac      120
ggaggtaacc agctagaggt acggctggac agagaataca agccaagtag tgtctggtgt      180
agcagctggt tatatccgat tcataagaag agtggtggat ggtttaggct atggttcgat      240
gcagcagtgt tattgtctcc cttcaccagg tgcttcagcg atcgaatgat gttgtactat      300
gaccctgatt tggatgatta ccaaaatgct cctggtgtcc aaacccgggt tcctcatttc      360
ggttcgacca aatcacttct atacctcgac cctcgtctcc ggttagtact ttccaagata      420
tatcattttg ggacatttgc ataatgaaca aaatagacat aaatttgggg gattattgtt      480
atatcaatat ccatttatat gctagtcggt aatgtgagtg ttatgttagt atagttaatg      540
tgagtgttat gtgattttcc attttaaatg aagctagaaa gttgtcgttt aataatgttg      600
ctatgtcatg agaattataa ggacactatg taaatgtagc ttaataataa ggtttgattt      660
gcagagatgc cacatcttac atggaacatt tggtgaaagc tctagagaaa aaatgcgggt      720
atgttaacga ccaaaccatc ctaggagctc catatgattt caggtacggc ctggctgctt      780
cgggccaccc gtcccgtgta gcctcacagt tcctacaaga cctcaaacaa ttggtggaaa      840
aaactagcag cgagaacgaa ggaaagccag tgatactcct ctcccatagc ctaggaggac      900
ttttcgtcct ccatttcctc aaccgtacca cccttcatg gcgccgcaag tacatcaaac       960
actttgttgc actcgctgcg ccatggggtg ggacgatctc tcagatgaag acatttgctt     1020
ctggcaacac actcggtgtc cctttagtta accctttgct ggtcagacgg catcaggaga     1080
cctccgagag taaccaatgg ctacttccat ctaccaaagt gtttcacgac agaactaaac     1140
cgcttgtcgt aactccccag gttaactaca cagcttacga gatggatcgg ttttttgcag     1200
acattggatt ctcacaagga gttgtgcctt acaagacaag agtgttgcct ttaacagagg     1260
agctgatgac tccgggagtg ccagtcactt gcatatatgg gagaggagtt gatacaccgg     1320
aggttttgat gtatggaaaa ggaggattcg ataagcaacc agagattaag tatggagatg     1380
gagatgggac ggttaatttg gcgagcttag cagctttgaa agtcgatagc ttgaacaccg     1440
tagagattga tggagtttcg catacatcta tacttaaaga cgagatcgca cttaaagaga     1500
ttatgaagca gatttcaatt attaattatg aattagccaa tgttaatgcc gtcaatgaat     1560
ga                                                                   1562

<210> SEQ ID NO 11
<211> LENGTH: 3896
<212> TYPE: DNA
<213> ORGANISM: Arabidopsis thaliana

<400> SEQUENCE: 11
```

-continued

```
atgggagcga attcgaaatc agtaacggct tccttcaccg tcatcgccgt ttttttcttg      60
atttgcggtg gccgaactgc ggtggaggat gagaccgagt ttcacggcga ctactcgaag     120
ctatcgggta taatcattcc gggatttgcg tcgacgcagc tacgagcgtg gtcgatcctt     180
gactgtccat acactccgtt ggacttcaat ccgctcgacc tcgtatggct agacaccact     240
aaggtccgtg atcttcattt ccttcgctcc ttattctgtc ggtcgagtca cttgttgatg     300
aattccaagc gaaatatagc aatgaagcat gtctcgtctc tcttattgat tcgttcatta     360
gtcaacagtg acgcttctga atctgagttt agagtcatat aaaacagctg actcggcgag     420
tgtttcccat cgcttttggt tcgctaaatg tagcgcaatg aatgtgtaat tagtctgcgc     480
tttttattca actagatctg caagtttttc agagtgctca atagtagtta gaaaatgtta     540
ggtcatttta cttgtgcatt gtgattcttt tggttgttgc ttactgatcg acgtgatgga     600
tggtttacag cttctttctg ctgtcaactg ctggtttaag tgtatggtgc tagatcctta     660
taatcaaaca gaccatcccg agtgtaagtc acggcctgac agtggtcttt cagccatcac     720
agaattggat ccaggttaca taacaggtag tttcggattt ttctttcttt tgagttttct     780
tcaatttgat atcatcttgt tgtgatataa tatggctaag ttcattaatt tggtcaattt     840
tcaggtcctc tttctactgt ctggaaagag tggcttaagt ggtgtgttga gtttggtata     900
gaagcaaatg caattgtcgc tgttccatac gattggagat tgtcaccaac caaattggaa     960
gagcgtgacc tttactttca caagctcaag ttagtcctta tcaggctaat gtcttttatc    1020
ttctcttttt atgtaagata agctaagagc tctggtcgtc ttccttttg caggttgacc     1080
tttgaaactg ctttaaaact ccgtggcggc ccttctatag tatttgccca ttcaatgggt    1140
aataatgtct tcagatactt tctggaatgg ctgaggctag aaattgcacc aaaacattat    1200
ttgaagtggc ttgatcagca tatccatgct tatttcgctg ttggtaccgg cctactatcc    1260
ttaagttacc atttt atttt ttctctaatt gggggagtta tgttgtgact tactggattg    1320
agctcgatac ctgatttgtt gttgatttag gagctcctct tcttggttct gttgaggcaa    1380
tcaaatctac tctctctggt gtaacgtttg gccttcctgt ttctgaggtg acctctgact    1440
tctctttagt tttaagtagt tgatatcaac caggtcttat aactcactgg attttccttt    1500
tgaaagtatt acttttgtta attgaactgc tgtacgcgat atggtatctg tagatcttga    1560
agtgctagtt atcaaagaac atattgtggg tagtatacct gtcagcggcc ttagctaata    1620
caaccaaacc acatgtacac tgatttagtt ttcagattat tatggtagac tttaagttga    1680
gaagaaactt tgactgaaat cttttattt taataggcta tgatttgttt attgaaatca    1740
tgtgacatat tgcatgcgc ttctcatgtt ttttgttggc aaggcttcag ggaactgctc     1800
ggttgttgtc caattctttt gcgtcgtcat tgtggcttat gccatttca aagaattgca     1860
agggtgataa cacattctgg acgcattttt ctgggggtgc tgcaaagaaa gataagcgcg    1920
tataccactg tgatgaagag gaatatcaat caaaatattc tggctggccg acaaatatta    1980
ttaacattga aattccttcc actagcggtt agactctgta tatgcaactg taacactaac    2040
aaaagtttca ccaagaatgt tcactctcat atttcgttcc tttgatgtgt atccatcagt    2100
tacagaaaca gctctagtca acatgaccag catggaatgt ggccttccca cccttttgtc    2160
tttcacagcc cgtgaactag cagatgggac tcttttcaaa gcaatagaag actatgaccc    2220
agatagcaag aggatgttac accagttaaa gaagtacgta cctttctttg tgataagaaa    2280
tattgctcat cgatcatcac ttgctggctt cttgtacgtc aaattgtttt gtttaaatct    2340
ctatatcaat tgttcatatg ctttgtctttt cttactataa gaaacaagta aatcagaaa    2400
```

-continued

```
cctattatt gattatcagt tctctcctta tattatggaa tgtcttttc gtttacagtt      2460 atgaatgcaa aaggggtat tttagttgat tgattctctc attctctagt ttgttttgac     2520
taatagcgtc aattttgttt ttctagcaaa tctttgtgaa ttatatataa catgctaact    2580
atacttttca ggttgtatca tgatgaccct gttttaatc ctctgactcc ttgggagaga     2640
ccacctataa aaatgtatt ttgcatatat ggtgctcatc taaagacaga ggtatgatgc     2700
attctcaata tcacattatg cgttgacttt gttattatat tccccatttg gtttgcaata    2760 tcttttgaa ttatgattta tcttctccct tgcatcttat gctattaagc gttaaaggta     2820
ctaaatgtat gaagctgtct gtcataggtt ggttattact ttgccccaag tggcaaacct    2880
tatcctgata attggatcat cacggatatc atttatgaaa ctgaaggttc cctcgtgtca    2940
aggtaatttt ccgcaatggc agaagtaaaa caggaaggca aagtcttctg tatcagtcta    3000
gtggcatgtt atctcagttg cataagcaaa ttattaaaca actaaaattt aagtactttt    3060
ttatcattcc ttttgagctt agtggatgat cagtggctta agtgggaag aggtgttgca     3120 tgaaacatga cacttgtatc aaagataact agcaaaacaa aactaaccca tttctgaatt    3180
tcatattatt aggagtagtc gtgcttttaa aaaatttgtt ttaagaaacc gaaaaactag    3240
ttcatatctt gattgtgcaa tatctgcagg tctggaactg tggttgatgg aacgctgga     3300 cctataactg gggatgagac ggtaagctca gaagttggtt ttgaaattat cttcttgcaa    3360
actactgaag actaagataa acttgcttc tggaacactg cttgctatgt tctctagtac     3420
actgcaatat tgactctccg ctactttat tgattatgaa attgatctct tataggtacc     3480
ctatcattca ctctcttggt gcaagaattg gctcggacct aaagttaaca taacaatggc    3540
tccccaggta ctctttttta gttcctcacc ttatatagat caaactttaa gtgtactttt    3600
ctggttatgt gttgatttac ctccaatttg ttctttctaa aaatcatata tctctgtact    3660
cctcaagaac ttgtattaat ctaaacgaga ttctcattgg gaaaataaaa caacagccag    3720
aacacgatgg aagcgacgta catgtggaac taaatgttga tcatgagcat gggtcagaca    3780
tcatagctaa catgacaaaa gcaccaaggg ttaagtacat aaccttttat gaagactctg    3840
agagcattcc ggggaagaga accgcagtct gggagcttga taaaagtggg tattaa        3896
```

<210> SEQ ID NO 12
<211> LENGTH: 709
<212> TYPE: DNA
<213> ORGANISM: Lycopersicon esculentum

<400> SEQUENCE: 12

```
ctggggccaa aagtgaacat aacaaggaca ccacagtcag agcatgatgt tcagatgtac      60
aagtgcatct aaatatagag catcaacatg gtgaagatat cattcccaat atgacaaagt     120
tacctacaat gaagtacata acctattatg aggattctga agttttcca gggacaagaa      180 cagcagtttg ggagcttgat aaagcaaatc acaggaacat tgtcagatct ccagctttga     240
tgcgggagct gtggcttgag atgtggcatg atattcatcc tgataaaaag tccaagtttg     300
ttacaaaagg tggtgtctga tcctcactat tttcttctat aaatgtttga gtttgtattg     360
acattgtaag tattgcaaca aaaagcaaag cgtgggcctc tgagggatga ggactgctat     420
tgggattacg ggaaagctcg atgtgcatgg gctgaacatt gtgaatacag gttagaatat     480
tcaaattata ttttgcaaaa tattctcttt ttgtgtattt aggccacctt tccccggtca     540
caacgatgca gatatgtatt cggggatgtt cacctgggac agagttgcag attgaagagt     600
```

-continued

```
tctacatctc acatcctgtc acactatgtg tgatatttaa gaaactttgt ttggcggaac    660
aacaagtttg cacaaacatt tgaagaagaa agcgaaatga ttcagagag              709
```

<210> SEQ ID NO 13
<211> LENGTH: 623
<212> TYPE: PRT
<213> ORGANISM: Schizosaccharomyces pombe

<400> SEQUENCE: 13

```
Met Ala Ser Ser Lys Lys Ser Lys Thr His Lys Lys Lys Lys Glu Val
 1               5                  10                  15

Lys Ser Pro Ile Asp Leu Pro Asn Ser Lys Lys Pro Thr Arg Ala Leu
            20                  25                  30

Ser Glu Gln Pro Ser Ala Ser Glu Thr Gln Ser Val Ser Asn Lys Ser
        35                  40                  45

Arg Lys Ser Lys Phe Gly Lys Arg Leu Asn Phe Ile Leu Gly Ala Ile
    50                  55                  60

Leu Gly Ile Cys Gly Ala Phe Phe Phe Ala Val Gly Asp Asp Asn Ala
65                  70                  75                  80

Val Phe Asp Pro Ala Thr Leu Asp Lys Phe Gly Asn Met Leu Gly Ser
                85                  90                  95

Ser Asp Leu Phe Asp Asp Ile Lys Gly Tyr Leu Ser Tyr Asn Val Phe
            100                 105                 110

Lys Asp Ala Pro Phe Thr Thr Asp Lys Pro Ser Gln Ser Pro Ser Gly
        115                 120                 125

Asn Glu Val Gln Val Gly Leu Asp Met Tyr Asn Glu Gly Tyr Arg Ser
    130                 135                 140

Asp His Pro Val Ile Met Val Pro Gly Val Ile Ser Ser Gly Leu Glu
145                 150                 155                 160

Ser Trp Ser Phe Asn Asn Cys Ser Ile Pro Tyr Phe Arg Lys Arg Leu
                165                 170                 175

Trp Gly Ser Trp Ser Met Leu Lys Ala Met Phe Leu Asp Lys Gln Cys
            180                 185                 190

Trp Leu Glu His Leu Met Leu Asp Lys Lys Thr Gly Leu Asp Pro Lys
        195                 200                 205

Gly Ile Lys Leu Arg Ala Ala Gln Gly Phe Glu Ala Ala Asp Phe Phe
    210                 215                 220

Ile Thr Gly Tyr Trp Ile Trp Ser Lys Val Ile Glu Asn Leu Ala Ala
225                 230                 235                 240

Ile Gly Tyr Glu Pro Asn Asn Met Leu Ser Ala Ser Tyr Asp Trp Arg
                245                 250                 255

Leu Ser Tyr Ala Asn Leu Glu Glu Arg Asp Lys Tyr Phe Ser Lys Leu
            260                 265                 270

Lys Met Phe Ile Glu Tyr Ser Asn Ile Val His Lys Lys Lys Val Val
        275                 280                 285

Leu Ile Ser His Ser Met Gly Ser Gln Val Thr Tyr Tyr Phe Phe Lys
    290                 295                 300

Trp Val Glu Ala Glu Gly Tyr Gly Asn Gly Pro Thr Trp Val Asn
305                 310                 315                 320

Asp His Ile Glu Ala Phe Ile Asn Ile Ser Gly Ser Leu Ile Gly Ala
                325                 330                 335

Pro Lys Thr Val Ala Ala Leu Leu Ser Gly Glu Met Lys Asp Thr Gly
            340                 345                 350

Ile Val Ile Thr Leu Asn Ile Leu Glu Lys Phe Phe Ser Arg Ser Glu
```

```
                355                 360                 365
Arg Ala Met Met Val Arg Thr Met Gly Gly Val Ser Ser Met Leu Pro
    370                 375                 380

Lys Gly Gly Asp Val Ala Pro Asp Asp Leu Asn Gln Thr Asn Phe Ser
385                 390                 395                 400

Asn Gly Ala Ile Ile Arg Tyr Arg Glu Asp Ile Asp Lys Asp His Asp
                405                 410                 415

Glu Phe Asp Ile Asp Asp Ala Leu Gln Phe Leu Lys Asn Val Thr Asp
            420                 425                 430

Asp Asp Phe Lys Val Met Leu Ala Lys Asn Tyr Ser His Gly Leu Ala
        435                 440                 445

Trp Thr Glu Lys Glu Val Leu Lys Asn Asn Glu Met Pro Ser Lys Trp
    450                 455                 460

Ile Asn Pro Leu Glu Thr Ser Leu Pro Tyr Ala Pro Asp Met Lys Ile
465                 470                 475                 480

Tyr Cys Val His Gly Val Gly Lys Pro Thr Glu Arg Gly Tyr Tyr Tyr
                485                 490                 495

Thr Asn Asn Pro Glu Gly Gln Pro Val Ile Asp Ser Ser Val Asn Asp
            500                 505                 510

Gly Thr Lys Val Glu Asn Gly Ile Val Met Asp Asp Gly Asp Gly Thr
        515                 520                 525

Leu Pro Ile Leu Ala Leu Gly Leu Val Cys Asn Lys Val Trp Gln Thr
    530                 535                 540

Lys Arg Phe Asn Pro Ala Asn Thr Ser Ile Thr Asn Tyr Glu Ile Lys
545                 550                 555                 560

His Glu Pro Ala Ala Phe Asp Leu Arg Gly Gly Pro Arg Ser Ala Glu
                565                 570                 575

His Val Asp Ile Leu Gly His Ser Glu Leu Asn Glu Ile Ile Leu Lys
            580                 585                 590

Val Ser Ser Gly His Gly Asp Ser Val Pro Asn Arg Tyr Ile Ser Asp
        595                 600                 605

Ile Gln Glu Ile Ile Asn Glu Ile Asn Leu Asp Lys Pro Arg Asn
    610                 615                 620

<210> SEQ ID NO 14
<211> LENGTH: 432
<212> TYPE: PRT
<213> ORGANISM: Arabidopsis thaliana

<400> SEQUENCE: 14

Met Lys Lys Ile Ser Ser His Tyr Ser Val Val Ile Ala Ile Leu Val
1               5                   10                  15

Val Val Thr Met Thr Ser Met Cys Gln Ala Val Gly Ser Asn Val Tyr
            20                  25                  30

Pro Leu Ile Leu Val Pro Gly Asn Gly Asn Gln Leu Glu Val Arg
        35                  40                  45

Leu Asp Arg Glu Tyr Lys Pro Ser Ser Val Trp Cys Ser Ser Trp Leu
    50                  55                  60

Tyr Pro Ile His Lys Lys Ser Gly Gly Trp Phe Arg Leu Trp Phe Asp
65                  70                  75                  80

Ala Ala Val Leu Leu Ser Pro Phe Thr Arg Cys Phe Ser Asp Arg Met
                85                  90                  95

Met Leu Tyr Tyr Asp Pro Asp Leu Asp Asp Tyr Gln Asn Ala Pro Gly
            100                 105                 110
```

-continued

```
Val Gln Thr Arg Val Pro His Phe Gly Ser Thr Lys Ser Leu Leu Tyr
            115                 120                 125

Leu Asp Pro Arg Leu Arg Asp Ala Thr Ser Tyr Met Glu His Leu Val
130                 135                 140

Lys Ala Leu Glu Lys Lys Cys Gly Tyr Val Asn Asp Gln Thr Ile Leu
            145                 150                 155                 160

Gly Ala Pro Tyr Asp Phe Arg Tyr Gly Leu Ala Ala Ser Gly His Pro
                165                 170                 175

Ser Arg Val Ala Ser Gln Phe Leu Gln Asp Leu Lys Gln Leu Val Glu
            180                 185                 190

Lys Thr Ser Ser Glu Asn Glu Gly Lys Pro Val Ile Leu Leu Ser His
        195                 200                 205

Ser Leu Gly Gly Leu Phe Val Leu His Phe Leu Asn Arg Thr Thr Pro
    210                 215                 220

Ser Trp Arg Arg Lys Tyr Ile Lys His Phe Val Ala Leu Ala Ala Pro
225                 230                 235                 240

Trp Gly Gly Thr Ile Ser Gln Met Lys Thr Phe Ala Ser Gly Asn Thr
                245                 250                 255

Leu Gly Val Pro Leu Val Asn Pro Leu Leu Val Arg Arg His Gln Arg
            260                 265                 270

Thr Ser Glu Ser Asn Gln Trp Leu Leu Pro Ser Thr Lys Val Phe His
        275                 280                 285

Asp Arg Thr Lys Pro Leu Val Val Thr Pro Gln Val Asn Tyr Thr Ala
    290                 295                 300

Tyr Glu Met Asp Arg Phe Phe Ala Asp Ile Gly Phe Ser Gln Gly Val
305                 310                 315                 320

Val Pro Tyr Lys Thr Arg Val Leu Pro Leu Thr Glu Glu Leu Met Thr
                325                 330                 335

Pro Gly Val Pro Val Thr Cys Ile Tyr Gly Arg Gly Val Asp Thr Pro
            340                 345                 350

Glu Val Leu Met Tyr Gly Lys Gly Gly Phe Asp Lys Gln Pro Glu Ile
        355                 360                 365

Lys Tyr Gly Asp Gly Asp Gly Thr Val Asn Leu Ala Ser Leu Ala Ala
    370                 375                 380

Leu Lys Val Asp Ser Leu Asn Thr Val Glu Ile Asp Gly Val Ser His
385                 390                 395                 400

Thr Ser Ile Leu Lys Asp Glu Ile Ala Leu Lys Glu Ile Met Lys Gln
                405                 410                 415

Ile Ser Ile Ile Asn Tyr Glu Leu Ala Asn Val Asn Ala Val Asn Glu
            420                 425                 430
```

<210> SEQ ID NO 15
<211> LENGTH: 552
<212> TYPE: PRT
<213> ORGANISM: Arabidopsis thaliana

<400> SEQUENCE: 15

```
Met Gly Ala Asn Ser Lys Ser Val Thr Ala Ser Phe Thr Val Ile Ala
1               5                   10                  15

Val Phe Phe Leu Ile Cys Gly Gly Arg Thr Ala Val Glu Asp Glu Thr
                20                  25                  30

Glu Phe His Gly Asp Tyr Ser Lys Leu Ser Gly Ile Ile Ile Pro Gly
            35                  40                  45

Phe Ala Ser Thr Gln Leu Arg Ala Trp Ser Ile Leu Asp Cys Pro Tyr
        50                  55                  60
```

-continued

```
Thr Pro Leu Asp Phe Asn Pro Leu Asp Leu Val Trp Leu Asp Thr Thr
 65                  70                  75                  80

Lys Leu Leu Ser Ala Val Asn Cys Trp Phe Lys Cys Met Val Leu Asp
                 85                  90                  95

Pro Tyr Asn Gln Thr Asp His Pro Glu Cys Lys Ser Arg Pro Asp Ser
            100                 105                 110

Gly Leu Ser Ala Ile Thr Glu Leu Asp Pro Gly Tyr Ile Thr Gly Pro
            115                 120                 125

Leu Ser Thr Val Trp Lys Glu Trp Leu Lys Trp Cys Val Glu Phe Gly
            130                 135                 140

Ile Glu Ala Asn Ala Ile Val Ala Val Pro Tyr Asp Trp Arg Leu Ser
145                 150                 155                 160

Pro Thr Lys Leu Glu Glu Arg Asp Leu Tyr Phe His Lys Leu Lys Leu
                165                 170                 175

Thr Phe Glu Thr Ala Leu Lys Leu Arg Gly Gly Pro Ser Ile Val Phe
            180                 185                 190

Ala His Ser Met Gly Asn Asn Val Phe Arg Tyr Phe Leu Glu Trp Leu
            195                 200                 205

Arg Leu Glu Ile Ala Pro Lys His Tyr Leu Lys Trp Leu Asp Gln His
            210                 215                 220

Ile His Ala Tyr Phe Ala Val Gly Ala Pro Leu Leu Gly Ser Val Glu
225                 230                 235                 240

Ala Ile Lys Ser Thr Leu Ser Gly Val Thr Phe Gly Leu Pro Val Ser
                245                 250                 255

Glu Gly Thr Ala Arg Leu Leu Ser Asn Ser Phe Ala Ser Ser Leu Trp
            260                 265                 270

Leu Met Pro Phe Ser Lys Asn Cys Lys Gly Asp Asn Thr Phe Trp Thr
            275                 280                 285

His Phe Ser Gly Gly Ala Ala Lys Lys Asp Lys Arg Val Tyr His Cys
            290                 295                 300

Asp Glu Glu Glu Tyr Gln Ser Lys Tyr Ser Gly Trp Pro Thr Asn Ile
305                 310                 315                 320

Ile Asn Ile Glu Ile Pro Ser Thr Ser Ala Arg Glu Leu Ala Asp Gly
                325                 330                 335

Thr Leu Phe Lys Ala Ile Glu Asp Tyr Asp Pro Asp Ser Lys Arg Met
            340                 345                 350

Leu His Gln Leu Lys Lys Tyr Val Pro Phe Phe Val Ile Arg Asn Ile
            355                 360                 365

Ala His Arg Ser Ser Leu Ala Gly Phe Leu Leu Tyr His Asp Asp Pro
            370                 375                 380

Val Phe Asn Pro Leu Thr Pro Trp Glu Arg Pro Pro Ile Lys Asn Val
385                 390                 395                 400

Phe Cys Ile Tyr Gly Ala His Leu Lys Thr Glu Val Gly Tyr Tyr Phe
                405                 410                 415

Ala Pro Ser Gly Lys Pro Tyr Pro Asp Asn Trp Ile Ile Thr Asp Ile
            420                 425                 430

Ile Tyr Glu Thr Glu Gly Ser Leu Val Ser Arg Ser Gly Thr Val Val
            435                 440                 445

Asp Gly Asn Ala Gly Pro Ile Thr Gly Asp Glu Thr Val Pro Tyr His
            450                 455                 460

Ser Leu Ser Trp Cys Lys Asn Trp Leu Gly Pro Lys Val Asn Ile Thr
465                 470                 475                 480
```

-continued

```
Met Ala Pro Gln Ile Leu Ile Gly Lys Ile Lys Gln Gln Pro Glu His
                485                 490                 495

Asp Gly Ser Asp Val His Val Glu Leu Asn Val Asp His Glu His Gly
            500                 505                 510

Ser Asp Ile Ile Ala Asn Met Thr Lys Ala Pro Arg Val Lys Tyr Ile
        515                 520                 525

Thr Phe Tyr Glu Asp Ser Glu Ser Ile Pro Gly Lys Arg Thr Ala Val
    530                 535                 540

Trp Glu Leu Asp Lys Ser Gly Tyr
545                 550

<210> SEQ ID NO 16
<211> LENGTH: 387
<212> TYPE: PRT
<213> ORGANISM: Arabidopsis thaliana

<400> SEQUENCE: 16

Val Gly Ser Asn Val Tyr Pro Leu Ile Leu Val Pro Gly Asn Gly Gly
 1               5                  10                  15

Asn Gln Leu Glu Val Arg Leu Asp Arg Glu Tyr Lys Pro Ser Ser Val
             20                  25                  30

Trp Cys Ser Ser Trp Leu Tyr Pro Ile His Lys Lys Ser Gly Gly Trp
         35                  40                  45

Phe Arg Leu Trp Phe Asp Ala Ala Val Leu Leu Ser Pro Phe Thr Arg
     50                  55                  60

Cys Phe Ser Asp Arg Met Met Leu Tyr Tyr Asp Pro Asp Leu Asp Asp
 65                  70                  75                  80

Tyr Gln Asn Ala Pro Gly Val Gln Thr Arg Val Pro His Phe Gly Ser
                 85                  90                  95

Thr Lys Ser Leu Leu Tyr Leu Asp Pro Arg Leu Arg Asp Ala Thr Ser
            100                 105                 110

Tyr Met Glu His Leu Val Lys Ala Leu Glu Lys Lys Cys Gly Tyr Val
        115                 120                 125

Asn Asp Gln Thr Ile Leu Gly Ala Pro Tyr Asp Phe Arg Tyr Gly Leu
    130                 135                 140

Ala Ala Ser Gly His Pro Ser Arg Val Ala Ser Gln Phe Leu Gln Asp
145                 150                 155                 160

Leu Lys Gln Leu Val Glu Lys Thr Ser Ser Glu Asn Glu Gly Lys Pro
                165                 170                 175

Val Ile Leu Leu Ser His Ser Leu Gly Gly Leu Phe Val Leu His Phe
            180                 185                 190

Leu Asn Arg Thr Thr Pro Ser Trp Arg Arg Lys Tyr Ile Lys His Phe
        195                 200                 205

Val Ala Leu Ala Ala Pro Trp Gly Gly Thr Ile Ser Gln Met Lys Thr
    210                 215                 220

Phe Ala Ser Gly Asn Thr Leu Gly Val Pro Leu Val Asn Pro Leu Leu
225                 230                 235                 240

Val Arg Arg His Gln Arg Thr Ser Glu Ser Asn Gln Trp Leu Leu Pro
                245                 250                 255

Ser Thr Lys Val Phe His Asp Arg Thr Lys Pro Leu Val Val Thr Pro
            260                 265                 270

Gln Val Asn Tyr Thr Ala Tyr Glu Met Asp Arg Phe Phe Ala Asp Ile
        275                 280                 285

Gly Phe Ser Gln Gly Val Val Pro Tyr Lys Thr Arg Val Leu Pro Leu
    290                 295                 300
```

```
Thr Glu Glu Leu Met Thr Pro Gly Val Pro Val Thr Cys Ile Tyr Gly
305                 310                 315                 320

Arg Gly Val Asp Thr Pro Glu Val Leu Met Tyr Gly Lys Gly Gly Phe
                325                 330                 335

Asp Lys Gln Pro Glu Ile Lys Tyr Gly Asp Gly Asp Gly Thr Val Asn
            340                 345                 350

Leu Ala Ser Leu Ala Ala Leu Lys Val Asp Ser Leu Asn Thr Val Glu
        355                 360                 365

Ile Asp Gly Val Ser His Thr Ser Ile Leu Lys Asp Glu Ile Ala Leu
370                 375                 380

Lys Glu Ile
385
```

<210> SEQ ID NO 17
<211> LENGTH: 389
<212> TYPE: PRT
<213> ORGANISM: Arabidopsis thaliana

<400> SEQUENCE: 17

```
Leu Lys Lys Glu Gly Leu Lys Ala Lys His Pro Val Val Phe Ile Pro
1               5                   10                  15

Gly Ile Val Thr Gly Gly Leu Glu Leu Trp Glu Gly Lys Gln Cys Ala
            20                  25                  30

Asp Gly Leu Phe Arg Lys Arg Leu Trp Gly Gly Thr Phe Leu Cys Trp
        35                  40                  45

Val Glu His Met Ser Leu Asp Asn Glu Thr Gly Leu Asp Pro Ala Gly
    50                  55                  60

Ile Arg Val Arg Ala Val Ser Gly Leu Val Ala Ala Asp Tyr Phe Ala
65                  70                  75                  80

Pro Gly Tyr Phe Val Trp Ala Val Leu Ile Ala Asn Leu Ala His Ile
                85                  90                  95

Gly Tyr Glu Glu Lys Asn Met Tyr Met Ala Ala Tyr Asp Trp Arg Leu
            100                 105                 110

Ser Phe Gln Asn Thr Glu Arg Asp Gln Thr Leu Ser Arg Met Lys Ser
        115                 120                 125

Asn Ile Glu Leu Met Val Ser Thr Asn Gly Gly Lys Lys Ala Val Ile
130                 135                 140

Val Pro His Ser Met Gly Val Leu Tyr Phe Leu His Phe Met Lys Trp
145                 150                 155                 160

Val Glu Ala Pro Ala Pro Leu Gly Gly Gly Gly Pro Asp Trp Cys
                165                 170                 175

Ala Lys Tyr Ile Lys Ala Val Met Asn Ile Gly Gly Pro Phe Leu Gly
            180                 185                 190

Val Pro Lys Ala Val Ala Gly Leu Phe Ser Ala Glu Ala Lys Asp Met
        195                 200                 205

Arg Met Thr Arg Thr Trp Asp Ser Thr Met Ser Met Leu Pro Lys Gly
210                 215                 220

Gly Asp Thr Ile Trp Gly Gly Leu Asp Trp Ser Pro Glu Leu Pro Asn
225                 230                 235                 240

Ala Pro Glu Met Glu Ile Tyr Ser Leu Tyr Gly Val Gly Ile Pro Thr
                245                 250                 255

Glu Arg Ala Tyr Val Tyr Lys Leu Asn Gln Ser Pro Asp Ser Cys Ile
            260                 265                 270

Pro Phe Gln Ile Phe Thr Ser Ala His Glu Glu Asp Glu Asp Ser Cys
```

-continued

```
                275                 280                 285
Leu Lys Ala Gly Val Tyr Asn Val Asp Gly Asp Glu Thr Val Pro Val
    290                 295                 300

Leu Ser Ala Gly Tyr Met Cys Ala Lys Ala Trp Arg Gly Lys Thr Arg
305                 310                 315                 320

Phe Asn Pro Ser Gly Ile Lys Thr Tyr Ile Arg Glu Tyr Asn His Ser
                325                 330                 335

Pro Pro Ala Asn Leu Leu Glu Gly Arg Gly Thr Gln Ser Gly Ala His
                340                 345                 350

Val Asp Ile Met Gly Asn Phe Ala Leu Ile Glu Asp Ile Met Arg Val
            355                 360                 365

Ala Ala Gly Gly Asn Gly Ser Asp Ile Gly His Asp Gln Val His Ser
    370                 375                 380

Gly Ile Phe Glu Trp
385

<210> SEQ ID NO 18
<211> LENGTH: 402
<212> TYPE: DNA
<213> ORGANISM: Arabidopsis thaliana
<220> FEATURE:
<221> NAME/KEY: CDS
<222> LOCATION: (120)..(401)
<220> FEATURE:
<221> NAME/KEY: Unsure
<222> LOCATION: 1..401
<223> OTHER INFORMATION: n is c, g, a, t or u.
<220> FEATURE:
<221> NAME/KEY: Unsure
<222> LOCATION: 1..401
<223> OTHER INFORMATION: Xaa = unknown

<400> SEQUENCE: 18
agaaacagct ctttgtctct ctcgactgat ctaacaatcc ctaatctgtg ttctaaattc      60
ctggacgaga tttgacaaag tccgtatagc ttaacctggt ttaatttcaa gtgacagat     119 atg ccc ctt att cat cgg aaa aag ccg acg gag aaa cca tcg acg ccg     167
Met Pro Leu Ile His Arg Lys Lys Pro Thr Glu Lys Pro Ser Thr Pro
  1               5                  10                  15 cca tct gaa gag gtg gtg cac gat gag gat tcg caa aag aaa cca cac     215
Pro Ser Glu Glu Val Val His Asp Glu Asp Ser Gln Lys Lys Pro His
             20                  25                  30 gaa tct tcc aaa tcc cac cat aag naa tcg aac gga gga ggg aag tgg     263
Glu Ser Ser Lys Ser His His Lys Xaa Ser Asn Gly Gly Gly Lys Trp
         35                  40                  45 tcg tgc atc gat tct tgt tgt tgg ttc att ggg tgt gtg tgt gta acc     311
Ser Cys Ile Asp Ser Cys Cys Trp Phe Ile Gly Cys Val Cys Val Thr
     50                  55                  60 tgg tgg ttt ctt ctc ttc ctt tac aac gca atg cct gcg agc ttc cct     359
Trp Trp Phe Leu Leu Phe Leu Tyr Asn Ala Met Pro Ala Ser Phe Pro
 65                  70                  75                  80 cag tat gta acg gag ccg aat cac gng tcc ttt gcc tta ccc g           402
Gln Tyr Val Thr Glu Pro Asn His Xaa Ser Phe Ala Leu Pro
                 85                  90

<210> SEQ ID NO 19
<211> LENGTH: 516
<212> TYPE: DNA
<213> ORGANISM: Neurospora crassa
<220> FEATURE:
<221> NAME/KEY: Unsure
<222> LOCATION: 1..516
<223> OTHER INFORMATION: n is g, c, a, t, or u.
```

```
<400> SEQUENCE: 19
ggtggcgaag acganggcgg aagttggagg ctaacgagaa tgacnctcgg agatggatct        60
accctctaga gacacgacta ccnttgcacc cagcctcaag gtntacngtt tntatgggta       120
ggaagccgac ggagcgagcc tacatctatc tggcgcccga tcccgggacg acaacgcatc       180
tttagatgac gatcgatacg actttgactn aggggcacat tgaccacggt gtgattttgg       240
gcgaaggcga tggcacagtg aaccttatga gtttggggta cctgtgcaat aagggtgga        300 aaatgaagag atacaatcct gcgggctcaa aaataaccgt ggtcgagatg ccgcatgaac       360
cagaacggtt caatccgaga ggagggccga atacggcgga cttaaatatg tagaaaaggt       420
tgaaatttat gaagagtaat taaatacggc acataggtta ctcaatagta tgactaatta       480
aaaaaaaatt tttttctaa aaaaaaaaaa aaaaaa                                  516

<210> SEQ ID NO 20
<211> LENGTH: 21
<212> TYPE: DNA
<213> ORGANISM: Artificial sequence
<220> FEATURE:
<223> OTHER INFORMATION: Description of artificial sequence: PCR primer

<400> SEQUENCE: 20
tctccatctt ctgcaaaacc t                                                  21

<210> SEQ ID NO 21
<211> LENGTH: 21
<212> TYPE: DNA
<213> ORGANISM: Artificial sequence
<220> FEATURE:
<223> OTHER INFORMATION: Description of artificial sequence: PCR primer

<400> SEQUENCE: 21
cctgtcaaaa accttctcct c                                                  21
```

METHODS OF MAKING TRIACYLGLYCEROL USING PHOSPHOLIPID:DIACYLGLYCEROL ACYLTRANSFERASE

The instant application claims the benefit of U.S. Provisional Application 60/180,687 filed Feb. 7, 2000, 60/132,010 filed Apr. 30, 1999 which is a continuation of U.S. Ser. No. 09/329,802, filed Jun. 10, 1999, now abandoned and claims foreign priority to EP 99106656.4, filed Apr. 1, 1999.

The present invention relates to the isolation, identification and characterization of recombinant DNA molecules encoding enzymes catalysing the transfer of fatty acids from phospholipids to diacylglycerol in the biosynthetic pathway for the production of triacylglycerol.

Triacylglycerol (TAG) is the most common lipid-based energy reserve in nature. The main pathway for synthesis of TAG is believed to involve three sequential acyl-transfers from acyl-CoA to a glycerol backbone (1, 2). For many years, acyl-CoA:diacylglycerol acyltransferase (DAGAT), which catalyzes the third acyl transfer reaction, was thought to be the only unique enzyme involved in TAG synthesis. It acts by diverting diacylglycerol (DAG) from membrane lipid synthesis into TAG (2). Genes encoding this enzyme were recently identified both in the mouse (3) and in plants (4, 5), and the encoded proteins were shown to be homologous to acyl-CoA: cholesterol acyltransferase (ACAT). It was also recently reported that another DAGAT exists in the oleaginous fungus *Mortierella ramanniana*, which is unrelated to the mouse DAGAT, the ACAT gene family or to any other known gene (6).

The instant invention relates to novel type of enzymes and their encoding genes for transformation. More specifically, the invention relates to use of a type of genes encoding a not previously described type of enzymes hereinafter designated phospholipid:diacylglycerol acyltransferases (PDAT), whereby this enzyme catalyses an acyl-CoA-independent reaction. The said type of genes expressed alone in transgenic organisms will enhance the total amount of oil (triacylglycerols) produced in the cells. The PDAT genes, in combination with a gene for the synthesis of an uncommon fatty acid will, when expressed in transgenic organisms, enhance the levels of the uncommon fatty acids in the triacylglycerols.

There is considerable interest world-wide in producing chemical feedstock, such as fatty acids, for industrial use from renewable plant resources rather than non-renewable petrochemicals. This concept has broad appeal to manufacturers and consumers on the basis of resource conservation and provides significant opportunity to develop new industrial crops for agriculture.

There is a diverse array of unusual fatty acids in oils from wild plant species and these have been well characterised. Many of these acids have industrial potential and this had led to interest in domesticating relevant plant species to enable agricultural production of particular fatty acids.

Development in genetic engineering technologies combined with greater understanding of the biosynthesis of unusual fatty acids now makes it possible to transfer genes coding for key enzymes involved in the synthesis of a particular fatty acid from a wild species into domesticated oilseed crops. In this way individual fatty acids can be produced in high purity and quantities at moderate costs.

In all crops like rape, sunflower, oilpalm etc., the oil (i.e. triacylglycerols) is the most valuable product of the seeds or fruits and other compounds like starch, protein, and fibre is regarded as by-products with less value. Enhancing the quantity of oil per weight basis at the expense of other compounds in oil crops would therefore increase the value of crop. If genes, regulating the allocation of reduced carbon into the production of oil can be up-regulated, the cells will accumulate more oil on the expense of other products. Such genes might not only be used in already high oil producing cells such as oil crops but could also induce significant oil production in moderate or low oil containing crops such as e.g. soy, oat, maize, potato, sugarbeats, and turnips as well as microorganisms.

SUMMARY OF THE INVENTION

Many of the unusual fatty acids of interest, e.g. medium chain fatty acids, hydroxy fatty acids, epoxy fatty acids and acetylenic fatty acids, have physical properties that are distinctly different from the common plant fatty acids. The present inventors have found that, in plant species naturally accumulating these uncommon fatty acids in their seed oil (i.e. triacylglycerol), these acids are absent, or present in very low amounts in the membrane (phospho)lipids of the seed. The low concentration of these acids in the membrane lipids is most likely a prerequisite for proper membrane function and thereby for proper cell functions. One aspect of the invention is that seeds of transgenic crops can be made to accumulate high amounts of uncommon fatty acids if these fatty acids are efficiently removed from the membrane lipids and channelled into seed triacylglycerols.

The inventors have identified a novel class of enzymes in plants catalysing the transfer of fatty acids from phospholipids to diacylglycerol in the production of triacylglycerol through an acyl-CoA-independent reaction and that these enzymes (phospholipid:diacylglycerol acyltransferases abbreviated as PDAT) are involved in the removal of hydroxylated, epoxygenated fatty acids, and probably also other uncommon fatty acids such as medium chain fatty acids, from phospholipids in plants.

This enzyme reaction was shown to be present in microsomal preparation from baker's yeast (*Saccharomyces cerevisiae*). The instant invention further pertains to an enzyme comprising an amino acid sequence as set forth in SEQ ID NO. 2 or a functional fragment, derivative, allele, homologous or isoenzyme thereof. A so called "knock out" yeast mutant, disrupted in the respective gene was obtained and microsomal membranes from the mutant was shown to totally lack PDAT activity. Thus, it was proved that the disrupted gene encodes for a PDAT enzyme (SEQ ID NO. 1 and 2).

Further genes and/or proteins of so far unknown function were identified and are contemplated within the scope of the instant invention. A gene from *Schizosaccharomyces pombe*, SPBC776.14 (SEQ ID NO. 3), a putative open reading frame CAA22887 of the SPBC776.14 (SEQ ID NO. 13) were identified. Further *Arabidopsis thaliana* genomic sequences (SEQ ID NO. 4, 10 and 11) coding for putative proteins were identified, as well as a putative open reading frame AAC80628 from the *A. thaliana* locus AC 004557 (SEQ ID NO. 14) and a putative open reading frame AAD10668 from the *A. thaliana* locus AC 003027 (SEQ ID NO. 15) were identified.

Also, partially sequenced cDNA clone from *Neurospora crassa* (SEQ ID NO. 9) and a *Zea mays* EST (Extended Sequence Tac) clone (SEQ ID NO. 7) and corresponding putative amino acid sequence (SEQ ID NO. 8) were identified. Finally, two cDNA clones were identified, one *Arabidopsis thaliana* EST (SEQ ID NO. 5) and corresponding predicted amino acid sequence SEQ ID NO. 6) and a *Lycopersicon esculentum* EST clone (SEQ ID NO. 12) were identified. Further, enzymes designated as PDAT comprising an amino acid sequence selected from the group consisting of sequences as set forth in SEQ ID NO. 16, 17 and 18 are contemplated within the scope of the invention. Moreover, an enzyme comprising an amino acid sequence encoded through a nucleotide sequence, a portion, derivative, allele or homologue thereof selected from the group consisting of sequences as set forth in SEQ ID NO. 1, 3, 4, 5, 7, 9, 10, 11, 12, 18 or 19 or a functional fragment, derivative, allele, homologue or isoenzyme of the enzyme encoding amino acid sequence are included within the scope of the invention.

A functional fragment of the instant enzyme is understood to be any polypeptide sequence which shows specific enzyme activity of a phospholipid:diacylglycerol acyltransferase (PDAT). The length of the functional fragment can for example vary in a range from about 660±10 amino acids to 660±250 amino acids, preferably from about 660±50 to 660±100 amino acids, whereby the "basic number" of 660 amino acids corresponds in this case to the polypeptide chain of the PDAT enzyme of SEQ ID NO. 2 encoded by a nucleotide sequence according to SEQ ID NO. 1. Consequently, the "basic number" of functional full length enzyme can vary in correspondance to the encoding nucleotide sequence.

A portion of the instant nucleotide sequence is meant to be any nucleotide sequence encoding a polypeptide which shows specific activity of a phospholipid:diacylglycerol acyltransferase (PDAT). The length of the nucleotide portion can vary in a wide range of about several hundreds of nucleotides based upon the coding region of the gene or a highly conserved sequence. For example the length varies in a range form about 1900±10 to 1900±1000 nucleotides, preferably form about 1900±50 to 1900±700 and more preferably from about 1900±100 to 1900±500 nucleotides, whereby the "basic number" of 1900 nucleotides corresponds in this case to the encoding nucleotide sequence of the PDAT enzyme of SEQ ID NO. 1. Consequently, the "basic number" of functional full length gene can vary.

An allelic variant of the instant nucleotide sequence is understood to be any different nucleotide sequence which encodes a polypeptide with a functionally equivalent function. The alleles pertain naturally occurring variants of the instant nucleotide sequences as well as synthetic nucleotide sequences produces by methods known in the art. Contemplated are even altered nucleotide sequences which result in an enzyme with altered activity and/or regulation or which is resistant against specific inhibitors. The instant invention further includes natural or synthetic mutations of the originally isolated nucleotide sequences. These mutations can be substitution, addition, deletion, inversion or insertion of one or more nucleotides.

A homologues nucleotide sequence is understood to be a complementary sequence and/or a sequence which specifically hybridizes with the instant nucleotide sequence. Hybridizing sequences include similar sequences selected from the group of DNA or RNA which specifically interact to the instant nucleotide sequences under at least moderate stringency conditions which are known in the art. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. This further includes short nucleotide sequences of e.g. 10 to 30 nucleotides, preferably 12 to 15 nucleotides. Included are also primer or hybridization probes.

A homologue nucleotide sequence included within the scope of the instant invention is a sequence which is at least about 40%, preferably at least about 50% or 60%, and more preferably at least about 70%, 80% or 90% and most preferably at least about 95%, 96%, 97%, 98% or 99% or more homologous to a nucleotide sequence of SEQ ID NO. 1.

All of the aforementioned definitions are true for amino acid sequences and functional enzymes and can easily transferred by a person skilled in the art.

Isoenzymes are understood to be enzymes which have the same or a similar substrate specifity and/or catalytic activity but a different primary structure.

In a first embodiment, this invention is directed to nucleic acid sequences that encode a PDAT. This includes sequences that encode biologically active PDATs as well as sequences that are to be used as probes, vectors for transformation or cloning intermediates. The PDAT encoding sequence may encode a complete or partial sequence depending upon the intended use. All or a portion of the genomic sequence, cDNA sequence, precursor PDAT or mature PDAT is intended.

Further included is a nucleotide sequence selected from the group consisting of sequences set forth in SEQ ID NO. 1, 3, 4, 10 or 11 or a portion, derivative, allele or homologue thereof. The invention pertains a partial nucleotide sequence corresponding to a full length nucleotide sequence selected from the group consisting of sequences set forth in SEQ ID NO. 5, 7, 9, 12, 18 or 19 or a portion, derivative, allele or homologue thereof. Moreover, a nucleotide sequence comprising a nucleotide sequence which is at least 40% homologous to a nucleotide sequence selected from the group consisting of those sequences set forth in SEQ ID NO. 1, 3, 4, 5, 7, 9, 10, 11, 12, 18 or 19 is contemplated within the scope of the invention.

The instant invention pertains to a gene construct comprising a said nucleotide sequences of the instant invention which is operably linked to a heterologous nucleic acid.

The term operably linked means a serial organisation e.g. of a promoter, coding sequence, terminator and/or further regulatory elements whereby each element can fulfill its original function during expression of the nucleotide sequence.

Further, a vector comprising of a said nucleotide sequence of the instant invention is contemplated in the instant invention. This includes also an expression vector as well as a vector further comprising a selectable marker gene and/or nucleotide sequences for the replication in a host cell and/or the integration into the genome of the host cell.

In a different aspect, this invention relates to a method for producing a PDAT in a host cell or progeny thereof, including genetically engineered oil seeds, yeast and moulds or any other oil accumulating organism, via the expression of a construct in the cell. Cells containing a PDAT as a result of the production of the PDAT encoding sequence are also contemplated within the scope of the invention.

Further, the invention pertains a transgenic cell or organism containing a said nucleotide sequence and/or a said gene construct and/or a said vector. The object of the instant invention is further a transgenic cell or organism which is an eucaryotic cell or organism. Preferably, the transgenic cell or organism is a yeast cell or a plant cell or a plant. The instant invention further pertains said transgenic cell or organism having an altered biosynthetic pathway for the production of triacylglycerol. A transgenic cell or organism having an altered oil content is also contemplated within the scope of this invention.

Further, the invention pertains a transgenic cell or organism wherein the activity of PDAT is altered in said cell or organism. This altered activity of PDAT is characterized by an alteration in gene expression, catalytic activity and/or regulation of activity of the enzyme. Moreover, a transgenic cell or organism is included in the instant invention, wherein the altered biosynthetic pathway for the production of triacylglycerol is characterized by the prevention of accumulation of undesirable fatty acids in the membrane lipids.

In a different embodiment, this invention also relates to methods of using a DNA sequence encoding a PDAT for increasing the oil-content within a cell.

Another aspect of the invention relates to the accommodation of high amounts of uncommon fatty acids in the triacylglycerol produced within a cell, by introducing a DNA sequence producing a PDAT that specifically removes these fatty acids from the membrane lipids of the cell and channel them into triacylglycerol. Plant cells having such a modification are also contemplated herein.

Further, the invention pertains a process for the production of triacylglycerol, comprising growing a said transgenic cell or organism under conditions whereby the said nucleotide sequence is expressed and whereby the said transgenic cells comprising an said enzyme catalysing the transfer of fatty acids from phospholipids to diacylglycerol forming triacylglycerol.

Moreover, triacylglycerols produced by the aforementioned process are included in scope of the instant invention.

Object of the instant invention is further the use of an instant nucleotide sequence and/or a said enzyme for the production of triacylglycerol and/or triacylglycerols with uncommon fatty acids. The use of a said instant nucleotide sequence and/or a said enzyme of the instant invention for the transformation of any cell or organism in order to be expressed in this cell or organism and result in an altered, preferably increased oil content of this cell or organism is also contemplated within the scope of the instant invention.

A PDAT of this invention includes any sequence of amino acids, such as a protein, polypeptide or peptide fragment obtainable from a microorganism, animal or plant source that demonstrates the ability to catalyse the production of triacylglycerol from a phospholipid and diacylglycerol under enzyme reactive conditions. By "enzyme reactive conditions" is meant that any necessary conditions are available in an environment (e.g., such factors as temperature, pH, lack of inhibiting substances) which will permit the enzyme to function.

Other PDATs are obtainable from the specific sequences provided herein. Furthermore, it will be apparent that one can obtain natural and synthetic PDATs, including modified amino acid sequences and starting materials for synthetic-protein modelling from the exemplified PDATs and from PDATs which are obtained through the use of such exemplified sequences. Modified amino acid sequences include sequences that have been mutated, truncated, increased and the like, whether such sequences were partially or wholly synthesised. Sequences that are actually purified from plant preparations or are identical or encode identical proteins thereto, regardless of the method used to obtain the protein or sequence, are equally considered naturally derived.

Further, the nucleic acid probes (DNA and RNA) of the present invention can be used to screen and recover "homologous" or "related" PDATs from a variety of plant and microbial sources.

Further, it is also apparent that a person skilled in the art can, with the information provided in this application, in any organism identify a PDAT activity, purify an enzyme with this activity and thereby identify a "non-homologues" nucleic acid sequence encoding such an enzyme.

The present invention can be essentially characterized by the following aspects:

1. Use of a PDAT gene (genomic clone or cDNA) for transformation.
2. Use of a DNA molecule according to item 1 wherein said DNA is used for transformation of any organism in order to be expressed in this organism and result in an active recombinant PDAT enzyme in order to increase oil content of the organism.
3. Use of a DNA molecule of item 1 wherein said DNA is used for transformation of any organism in order to prevent the accumulation of undesirable fatty acids in the membrane lipids.
4. Use according to item 1, wherein said PDAT gene is used for transforming transgenic oil accumulating organisms engineered to produce any uncommon fatty acid which is harmful if present in high amounts in membrane lipids, such as medium chain fatty acids, hydroxylated fatty acids, epoxygenated fatty acids and acetylenic fatty acids.
5. Use according to item 1, wherein said PDAT gene is used for transforming organisms, and wherein said organisms are crossed with other oil accumulating organisms engineered to produce any uncommon fatty acid which is harmful if present in high amounts in membrane lipids, comprising medium chain fatty acids, hydroxylated fatty acids, epoxygenated fatty acids and acetylenic fatty acids.
6. Use according to item 1, wherein the enzyme encoded by said PDAT gene of cDNA is coding for a PDAT with distinct acyl specificity.
7. Use according to item 1 wherein said PDAT encoding gene or cDNA, is derived from *Saccharomyces cereviseae,* or contain nucleotide sequences coding for an amino acid sequence 30% or more identical to the amino acid sequence of PDAT as presented in SEQ ID NO. 2.
8. Use according to item 1 wherein said PDAT encoding gene or cDNA is derived from *Saccharomyces cereviseae,* or contain nucleotide sequences coding for an amino acid sequence 40% or more identical to the amino acid sequence of PDAT as presented in SEQ ID NO. 2.
9. Use according to item 1 wherein said PDAT encoding gene or cDNA is derived from *Saccharomyces cereviseae,* or contain nucleotide sequences coding for an amino acid sequence 60% or more identical to the amino acid sequence of PDAT as presented in SEQ ID NO. 2.
10. Use according to item 1 wherein said PDAT encoding gene or cDNA is derived from *Saccharomyces cereviseae,* or contain nucleotide sequences coding for an amino acid sequence 80% or more identical to the amino acid sequence of PDAT as presented in SEQ ID NO.2.
11. Use according to item 1 wherein said PDAT encoding gene or cDNA is derived from plants or contain nucleotide sequences coding for an amino acid sequence 40% or more identical to the amino acid sequence of PDAT from *Arabidopsis thaliana* or to the protein encoded by the full length counterpart of the partial *Zea mays, Lycopericon esculentum,* or *Neurospora crassa* cDNA clones.
12. Transgenic oil accumulating organisms comprising, in their genome, a PDAT gene transferred by recombinant DNA technology or somatic hybridization.
13. Transgenic oil accumulating organisms according to item 12 comprising, in their genome, a PDAT gene having specificity for substrates with a particular uncommon fatty acid and the gene for said uncommon fatty acid.
14. Transgenic organisms according to item 12 or 13 which are selected from the group consisting of fungi, plants and animals.

15. Transgenic organisms according to item 12 or 13 which are selected from the group of agricultural plants.
16. Transgenic organisms according to item 12 or 13 which are selected from the group of agricultural plants and where said PDAT gene is expressed under the control of a storage organ specific promotor.
17. Transgenic organisms according to item 12 or 13 which are selected from the group of agricultural plants and where said PDAT gene is expressed under the control of a seed promotor.
18. Oils from organisms according to item 12-17.
19. A method for altering acyl specificity of a PDAT by alteration of the nucleotide sequence of a naturally occurring encoding gene and as a consequence of this alternation creating a gene encoding for an enzyme with novel acyl specifity.
20. A protein encoded by a DNA molecule according to item 1 or a functional fragment thereof.
21. A protein of item 20 designated phospholipid:diacylglycerol acyltransferase.
22. A protein of item 21 which has a distinct acyl specificity.
23. A protein of item 13 having the amino acid sequence as set forth in SEQ ID NO. 2, 13, 14 or 15 (and the proteins encoded by the full length or partial genes set forth in SEQ. ID. NO. 1, 3, 4, 5, 7, 9, 10, 11 or 12) or an amino acid sequence with at least 30% homology to said amino acid sequence.
24. A protein of item 23 isolated from *Saccharomyces cereviseae*.

DESCRIPTION OF FIGURES

FIG. 1:

Figure 2:
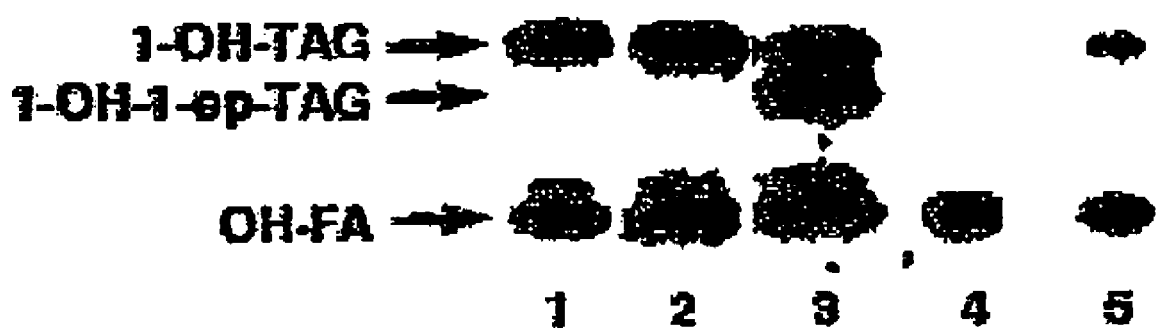

Metabolism of $^{14}C$-labeled PC into the neutral lipid fraction by plant microsomes. (A) Microsomes from developing seeds of sunflower, *R. communis* and *C. palaestina* were incubated for 80 mi at 30° C. with PC (8 nmol) having oleic acid in its sn-1 position, and either $^{14}C$-labeled oleic, ricinoleic or vernolic acid in its sn-2 position. Radioactivity incorporated in TAG (open bars), DAG (solid bars), and unsterified fatty acids (hatched bars) was quantified using thin layer chromatography followed by electronic autoradiography, and is shown as percentage of added labeled substrate. (B) Synthesis in vitro of TAG carrying two vernoloyl and one [$^{14}C$] ricinoleoyl group by microsomes from *R. communis*. The substrates added were unlabeled divernoloyl-DAG (5 nmol), together with either sn-1-oleoyl-sn-2-[$^{14}C$] ricinoleoyl-DAG (0.4 nmol, 770 dpm/nmol) or sn-1-oleoyl-sn-2-[$^{14}C$] ricinoleoyl-PC (0.4 nmol, 7700 dpm/nmol). The microsomes were incubated with the substrates for 30 min at 30° C., after which samples were removed for lipid analysis as described in the section "general methods". The data shown are the average of two experiments.

FIG. 2:

PDAT activity in yeast microsomes, as visualized by autoradiogram of neutral lipid products separated on TLC. Microsomal membranes (10 nmol of PC) from the wild type yeast strain FY1679 (lanes 1-3), a congenic yeast strain (FVKT004-04C(AL)) that is disrupted for YNR008w (lane 4) or the same disruption strain transformed with the plasmid pUS1, containing the YNR008w gene behind its native promoter (lane 5), were assayed for PDAT activity. As substrates, we used 2 nmol sn-1-oleoyl-sn-2-[$^{14}C$] ricinoleoyl-PC together with either 5 nmol of dioleoyl-DAG (lanes 2, 4 and 5) or rac-oleoyl-vernoleoyl-DAG (lane 3). The enzymatic assay and lipid analysis was performed as described in Materials and Methods. The cells were precultured for 20 h in liquid YPD medium, harvested and re-suspended in an equal volume of minimal medium (19) containing 16 g/l glycerol. The cells were then grown for an additional 24 h prior to being harvested. Selection for the plasmid was maintained by growing the transformed cells in synthetic medium lacking uracil (18). Abbreviations: 1-OH-TAG, monoricinoleoyl-TAG; 1-OH-1-ep-TAG, monoricinoleoyl-monovernoloyl-TAG; OH-FA, unesterified ricinoleic acid.

FIG. 3:

Lipid content (A, B) and PDAT activity (C) in PDAT overexpressing yeast cells. The PDAT gene in the plasmid pUS4 was overexpressed from the galactose-induced GAL1-TPK2 promoter in the wild type strain W303-1A (7). Its expression was induced after (A) 2 hours or (B) 25 hours of growth by the addition of 2% final concentration (w/v) of galactose. The cells were then incubated for another 22 hours before being harvested. The amount of lipids of the harvested cells was determined by GLC-analysis of its fatty acid contents and is presented as μmol fatty acids per mg dry weight in either TAG (open bar), polar lipids (hatched bar), sterol esters (solid bar) and other lipids (striped bar). The data shown are the mean values of results with three independent yeast cultures. (C) In vitro synthesis of TAG by microsomes prepared from yeast cells containing either the empty vector (vector) or the PDAT plasmid (+PDAT). The cells were grown as in FIG. 3A. The substrate lipids dioleoyl-DAG (2.5 nmol) and sn-1-oleoyl-sn-2-[$^{14}C$] ricinoleoyl-PC (2 nmol) were added to aliquots of microsomes (10 nmol PC), which were then incubated for 10 min at 28° C. The amount of label incorporated into TAG was quantified by electronic autoradiography. The results shown are the mean values of to experiments.

FIG. 4:

Substrate specificity of yeast PDAT. The PDAT activity was assayed by incubating aliquots of lyophilized microsomes (10 nmol PC) with substrate lipids at 30° C. for 10 min (panel A) or 90 min (panel B). Unlabeled DAG (2.5 nmol) was used as substrates together with different labeled phospholipids, as shown in the figure. (A) Sn-position specificity of yeast PDAT regarding the acyl donor substrate. Dioleoyl-DAG together with either sn-1-[$^{14}C$] oleoyl-sn-2-[$^{14}C$] oleoyl-PC (di-[$^{14}C$]-PC), sn-1-[$^{14}C$] oleoyl-sn-2-oleoyl-PC (sn-1-[$^{14}C$]-PC) or sn-1-oleoyl-sn-2-[$^{14}C$]oleoyl-PC (sn-2-[$^{14}C$]-PC). (B) Specificity of yeast PDAT regarding phospholipid headgroup and of the acyl composition of the phospholipid as well as of the diacylglycerol. Dioleoyl-DAG together with either sn-1-oleoyl-sn-2-[$^{14}C$]oleoyl-PC (oleoyl-PC), sn-1-oleoyl-sn-2-[$^{14}C$]oleoyl-PE (oleoyl-PE), sn-1-oleoyl-sn-2-[$^{14}C$] ricinoleoyl-PC (ricinoleoyl-PC) or sn-1-oleoyl-sn-2-[$^{14}C$] vernoloyl-PC (vernoloyl-PC). In the experiments presented in the 2 bars to the far right, monoricinoleoyl-DAG (ricinoleoyl-DAG or mono-vernoloyl-DAG (vernoloyl-DAG) were used together with sn-1-oleoyl-sn-2-[$^{14}C$]oleoyl-PC. The labeled that was incorporated into TAG (solid bars) and lyso-PC (LPC, open bars) was quantified by electronic autoradiography. The results shown are the mean values of two experiments. The microsomes used were from W303-1A cells overexpressing the PDAT gene from the GAL1-TPK2 promoter, as described in FIG. 3. The expression was induced at early stationary phase and the cells were harvested after an additional 24 h.

TAB. 1:

In vitro synthesis of triacylglycerols in microsomal preparations of developing castor bean. Aliquots of microsomes (20 nmol PC) were lyophilised and substrate lipids were added in benzene solution: (A) 0.4 nmol [$^{14}C$]-DAG (7760 dpm/nmol) and where indicated 1.6 nmol unlabeled DAG;

(B) 0.4 nmol [$^{14}$C]-DAG (7760 dpm/nmol) and 5 nmol unlabeled di-ricinoleoyl-PC and (C) 0.25 nmol [$^{14}$C]-PC (4000 dpm/nmol) and 5 nmol unlabeled DAG. The benzene was evaporated by $N_2$ and 0.1 ml of 50 mM potassium phosphate was added, thoroughly mixed and incubated at 30° C. for (A) 20 min.; (B) and (C) 30 min. Assays were terminated by extraction of the lipids in chloroform. The lipids were then separated by thin layer chromatography on silica gel 60 plates (Merck; Darmstadt, Germany) in hexan/diethlether/acetic 35:70:1.5. The radioactive lipids were visualized and the radioactivity quantified on the plate by electronic autoradiography (Instant Imager, Packard, U.S.). Results are presented as mean values of two experiments.

Radioactivity in different triacylglycerols (TAG) species formed. Abbreviations used: 1-OH—, mono-ricinoleoyl-; 2-OH, di-ricinoleoyl-; 3-OH—, triricinoleoyl; 1-OH-1-ver-, mono-ricinoleoyl-monovernoleoyl-; 1-OH-2-ver-, mono-ricinoleoyl-divernoleoyl-. Radiolabeled DAG and PC were prepared enzymatically. The radiolabeled ricinoleoyl group is attached at the sn-2-position of the lipid and unlabeled oleoyl group at the sn-1-position. Unlabeled DAG with vernoleoyl -or ricinoleoyl chains were prepared by the action of TAG lipase (6) on oil of *Euphorbia lagascae* or Castor bean, respectively. Synthetic di-ricinoleoyl-PC was kindly provided from Metapontum Agribios (Italy).

TAB. 2:

Total fatty acids per mg of T2 seeds pooled from individual *Arabidopsis thaliana* plants transformed with yeast PDAT gene under the control of napin promoter (26-14) or transformed with empty vector (32-4).

*=statistical difference between control plants and PDAT transformed plants in a mean different two-sided test at α=5.

DESCRIPTION OF THE SEQ ID:

SEQ ID NO. 1: Genomic DNA sequence and suggested amino acid sequence of the *Saccharomyces cerevisiae* PDAT gene, YNR008w, with GenBank accession number Z71623 and Y13139, and with nucleotide ID number 1302481.

SEQ ID NO. 2: The amino acid sequence of the suggested open reading frame YNR008m from *Saccharomyces cerevisiae*.

SEQ ID NO. 3: Genomic DNA sequence of the *Schizosaccharomyces pombe* geneSPBC776.14.

SEQ ID NO. 4: Genomic DNA sequence of part of the *Arabidopsis thaliana* locus with GenBank accession number AB006704.

SEQ ID NO. 5: Nucleotide sequence of the *Arabidopsis thaliana* cDNA clone with GenBank accession number T04806, and nucleotide ID number 315966.

SEQ ID NO. 6: Predicted amino acid sequence of the *Arabidopsis thaliana* cDNA clone with GenBank accession number T04806.

SEQ ID NO. 7: Nucleotide and amino acid sequence of the *Zea mays* EST clone with GenBank accession number AI461339, and nucleotide ID number g4288167.

SEQ ID NO. 8: Predicted amino acid sequence of the *Zea mays* EST clone with GenBank accession number AI461339, and nucleotide ID number g4288167.

SEQ ID NO. 9: DNA sequence of part of the *Neurospora crassa* EST clone W07G1, with GenBank accession number AI398644, and nucleotide ID number g4241729.

SEQ ID NO. 10: Genomic DNA sequence of part of the *Arabidopsis thaliana* locus with GenBank accession number AC004557.

SEQ ID NO. 11: Genomic DNA sequence of part of the *Arabidopsis thaliana* locus with GenBank accession number AC003027.

SEQ ID NO. 12: DNA sequence of part of the *Lycopersicon esculentum* cDNA clone with GenBank accession number AI486635.

SEQ ID NO. 13: Amino acid sequence of the *Schizosaccharomyces pombe* putative opening reading frame CAA22887 of the *Schizosaccharomyces pombe* gene SPBC776.14.

SEQ ID NO. 14: Amino acid sequence of the *Arabidopsis thaliana* putative open reading frame AAC80628 derived from the *Arabidopsis thaliana* locus with GenBank accession number AC004557.

SEQ ID NO. 15: Amino acid sequence of the *Arabidopsis thaliana* putative open reading frame AAD10668 derived from the *Arabidopsis thaliana* locus with GenBank accession number AC003027.

SEQ ID NO. 16: Amino acid sequence of the region of the *Arabidopsis thaliana* genomic sequence (AC004557).

SEQ ID NO. 17: Amino acid sequence of the region of the *Arabidopsis thaliana* genomic sequence (AB006704).

SEQ ID NO. 20: The amino acid sequence of the yeast ORF YNR008w sequence and amino acid sequence of the yeast ORF YNR008w from *Saccharomyces cerevisiae* derived from the corresponding genomic DNA sequence.

SEQ ID NO. 18: Nucleotide sequence and the corresponding amino acid sequence of the *Arabidopsis thaliana* EST-clone with GenBank accession number T04806, and ID number 315966.

SEQ ID NO. 19: DNA sequence of part of the *Neurospora crassa* cDNA clone WO7G1, ID number g4241729.

DETAILED DESCRIPTION OF THE INVENTION

General Methods

Yeast strains and plasmids. The wild type yeast strains used were either FY1679 (MATα his3-Δ200 leu2-Δ1 trp1-Δ6 ura3-52) or W303-1A (MATa ADE2-1 can1-100 his3-11,15 leu2-3,112 trp1-1 ura3-1) (7). The YNR008w::KanMX2 disruption strain FVKT004-04C(AL), which is congenic to FY1679, was obtained from the Euroscarf collection (8). A 2751 bp fragment containing the YNR008w gene with 583 bp of 5' and 183 bp of 3' flanking DNA was amplified from W303-1A genomic DNA using Taq polymerase with 5'-TCTCCATCTTCTGCAAAACCT-3' and 5'-CCTGT-CAAAAACCTTCTCCTC-3' as primers. The resulting PCR product was purified by agarose gel electrophoresis and cloned into the EcoRV site of pBluescript (pbluescript-pdat). For complementation experiments, the cloned fragment was released from pBluescript by HindIII-SacI digestion and then cloned between the HindIII and SacI sites of pFL39 (9), thus generating pUS1. For overexpression of the PDAT gene, a 2202 bp EcoRI fragment from the pBluescript plasmid which contains only 24 bp of 5' flanking DNA was cloned into the BamHI site of the GAL1-TPK2 expression vector pJN92 (12), thus generating pUS4.

Microsomal preparations. Microsomes from developing seeds of sunflower (*Helianthus annuus*), *Ricinus communis* and *Crepis palaestina* were prepared using the procedure of Stobart and Stymne (11). To obtain yeast microsomes, 1 g of yeast cells (fresh weight) was re-suspended in 8 ml of ice-cold buffer (20 mM Tris-Cl, pH 7.9, 10 mM $MgCl_2$, 1 mM EDTA, 5% (v/v) glycerol, 1 mM DTT, 0.3 M ammonium sulfate) in a 12 ml glass tube. To this tube, 4 ml of glass beads (diameter 0.45-0.5 mm) were added, and the tube was then heavily shaken (3×60 s) in an MSK cell homogenizer (B. Braun Melsungen AG, Germany). The homogenized suspension was centrifuged at 20,000×g for 15 min at 6° C. and the resulting supernatant was again centrifuged at 100,000×g for 2 h at 6° C. The 100,000×g pellet was resuspended in 0.1 M potassium phosphate (pH 7.2), and stored at −80° C. It is subsequently referred to as the crude yeast microsomal fraction.

Lipid substrates. Radio-labeled ricinoleic (12-hydroxy-octadecenoic) and vernolic (12,13-epoxy-octadecenoic) acids were synthesized enzymatically from [1-$^{14}$C]oleic acid and [1-$^{14}$C]linoleic acid, respectively, by incubation with microsomal preparations from seeds of Ricinus communis and Crepis palaestina, respectively (12). The synthesis of phosphatidylcholines (PC) or phosphatidylethanolamines (PE) with $^{14}$C-labeled acyl groups in the sn-2 position was performed using either enzymatic (13), or synthetic (14) acylation of [$^{14}$C]oleic, [$^{14}$C]ricinoleic, or [$^{14}$C]vernolic acid. Dioleoyl-PC that was labeled in the sn-1 position was synthesized from sn-1-[$^{14}$C]oleoyl-lyso-PC and unlabeled oleic acid as described in (14). Sn-1-oleoyl-sn-2-[$^{14}$C]ricinoleoyl-DAG was synthesized from PC by the action of phospholipase C type XI from B. Cereus (Sigma Chemical Co.) as described in (15). Monovernoloyl- and divernoleoyl-DAG were synthesized from TAG extracted from seeds of Euphorbia lagascae, using the TAG-lipase (Rizhopus arrhizus, Sigma Chemical Co.) as previously described (16). Monoricinoleoyl-TAG was synthesized according to the same method using TAG extracted from Castor bean.

Lipid analysis. Total lipid composition of yeast were determined from cells harvested from a 40 ml liquid culture, broken in a glass-bead shaker and extracted into chloroform as described by Bligh and Dyer (17), and then separated by thin layer chromatography in hexane/diethylether/acetic acid (80: 20:1) using pre-coated silica gel 60 plates (Merck). The lipid areas were located by brief exposure to $I_2$ vapors and identified by means of appropriate standards. Polar lipids, sterolesters and triacylglycerols, as well as the remaining minor lipid classes, referred to as other lipids, were excised from the plates. Fatty acid methylesters were prepared by heating the dry excised material at 85° C. for 60 min in 2% (v/v) sulfuric acid in dry methanol. The methyl esters were extracted with hexane and analyzed by GLC through a 50 m×0.32 mm CP-Wax58-CB fused-silica column (Chrompack), with methylheptadecanoic acid as an internal standard. The fatty acid content of each fraction was quantified and used to calculate the relative amount of each lipid class. In order to determine the total lipid content, 3 ml aliquots from yeast cultures were harvested by centrifugation and the resulting pellets were washed with distilled water and lyophilized. The weight of the dried cells was determined and the fatty acid content was quantified by GLC-analyses after conversion to methylesters as described above. The lipid content was then calculated as nmol fatty acid (FA) per mg dry weight yeast.

Enzyme assays. Aliquots of crude microsomal fractions (corresponding to 10 nmol of microsomal PC) from developing plant seeds or yeast cells were lyophilized over night. $^{14}$C-Labeled substrate lipids dissolved in benzene were then added to the dried microsomes. The benzene was evaporated under a stream of $N_2$, leaving the lipids in direct contact with the membranes, and 0.1 ml of 50 mM potassium phosphate (pH 7.2) was added. The suspension was thoroughly mixed and incubated at 30° C. for the time period indicated, up to 90 min. Lipids were extracted from the reaction mixture using chloroform and separated by thin layer chromatography in hexane/diethylether/acetic acid (35:70:1.5) using silica gel 60 plates (Merck). The radioactive lipids were visualized and quantified on the plates by electronic autoradiography (Instant Imager, Packard, US).

Yeast cultivation. Yeast cells were grown at 28° C. on a rotatory shaker in liquid YPD medium (1% yeast extract, 2% peptone, 2% glucose), synthetic medium (18) containing 2% (v/v) glycerol and 2% (v/v) ethanol, or minimal medium (19) containing 16 g/l of glycerol.

The instant invention is further characterized by the following examples which are not limiting:

Acyl-CoA-independent synthesis of TAG by oil seed microsomes. A large number of unusual fatty acids can be found in oil seeds (20). Many of these fatty acids, such as ricinoleic (21) and vernolic acids (22), are synthesized using phosphatidylcholin (PC) with oleoyl or linoleoyl groups esterified to the sn-2 position, respectively, as the immediate precursor. However, even though PC can be a substrate for unusual fatty acid synthesis and is the major membrane lipids in seeds, unusually fatty acids are rarely found in the membranes. Instead, they are mainly incorporated into the TAG. A mechanism for efficient and selective transfer of these unusual acyl groups from PC into TAG must therefore exist in oil seeds that accumulate such unusual fatty acids. This transfer reaction was biochemically characterized in seeds from castor bean (Ricinus communis) and Crepis palaestina, plants which accumulate high levels of ricinoleic and vernolic acid, respectively, and sunflower (Helianthus annuus), a plant which has only common fatty acids in its seed oil. Crude microsomal fractions from developing seeds were incubated with PC having $^{14}$C-labeled oleoyl, ricinoleoyl or vernoloyl groups at the sn-2 position. After the incubation, lipids were extracted and analyzed by thin layer chromatography. We found that the amount of radioactivity that was incorporated into the neutral lipid fraction increased linearly over a period of 4 hours (data not shown). The distribution of [$^{14}$C]acyl groups within the neutral lipid fraction was analyzed after 80 min (FIG. 1). Interestingly the amount and distribution of radioactivity between different neutral lipids were strongly dependent both on the plant species and on the type of [$^{14}$C] acyl chain. Thus, sunflower microsomes incorporated most of the label into DAG, regardless of the type of [$^{14}$C]acyl group. In contrast, R. communis microsomes preferentially incorporated [$^{14}$C]ricinoleoyl and [$^{14}$C]vernoloyl groups into DAG, while [$^{14}$C]oleyl groups mostly were found in DAG. C. palaestina microsomes, finally, incorporated only [$^{14}$C]vernolyol groups into TAG, with [$^{14}$C]ricinoleyl groups being found mostly as free fatty acids, and [$^{14}$C]oleyl groups in DAG. This shows that the high in vivo levels of ricinoleic acid and vernolic acid in the TAG pool of R. communis and C. palaestina, respectively, can be explained by an efficient and selective transfer of the corresponding acyl groups from PC to TAG in these organisms. The in-vitro synthesis of triacylglycerols in microsomal preparations of developing castor bean is summarized in table 1.

PDAT: a novel enzyme that catalyzes acyl-CoA-independent synthesis of TAG. It was investigated if DAG could serve both as an acyl donor as well as an acyl acceptor in the reactions catalyzed by the oil seed microsomes. Therefore, unlabeled divernoloyl-DAG was incubated with either sn-1-oleoyl-sn-2-[$^{14}$C]ricinoleoyl-DAG or sn-1-oleoyl-sn-2-[$^{14}$C] ricinoleoyl-PC in the presence of R. communis microsomes. The synthesis of TAG molecules containing both [$^{14}$C]ricinoleoyl and vernoloyl groups was 5 fold higher when [$^{14}$C] ricinoleoyl-PC served as acyl donor as compared to [$^{14}$C] ricinoleoyl-DAG (FIG. 1B). These data strongly suggests that PC is the immediate acyl donor and DAG the acyl acceptor in the acyl-CoA-independent formation of TAG by oil seed microsomes. Therefore, this reaction is catalyzed by a new enzyme which we called phospholipid:diacylglycerol acyltransferase (PDAT).

PDAT activity in yeast microsomes. Wild type yeast cells were cultivated under conditions where TAG synthesis is induced. Microsomal membranes were prepared from these cells and incubated with sn-2-[$^{14}$C]-ricinoleoyl-PC and DAG and the $^{14}$C-labeled products formed were analyzed. The PC-derived [$^{14}$C]ricinoleoyl groups within the neutral lipid fraction mainly were found in free fatty acids or TAG, and also that the amount of TAG synthesized was dependent on the amount of DAG that was added to the reaction (FIG. 2). The in vitro synthesis of TAG containing both ricinoleoyl and vernoloyl groups, a TAG species not present in vivo, from exogenous added sn-2-[$^{14}$C]ricinoleoyl-PC and unlabeled vernoloyl-DAG (FIG. 2, lane 3) clearly demonstrates the existence of an acyl-CoA-independent synthesis of TAG involving PC and DAG as substrates in yeast microsomal membranes. Consequently, TAG synthesis in yeast can be catalyzed by an enzyme similar to the PDAT found in plants.

The PDAT encoding gene in yeast. A gene in the yeast genome (YNR008w) is known, but nothing is known about the function of YNR008w, except that the gene is not essential for growth under normal circumstances. Microsomal membranes were prepared from the yeast strain FVKT004-04C (AL) (8) in which the gene with unknown function had been disrupted. PDAT activity in the microsomes were assayed using PC with radiolabelled fatty acids at the sn-2 position. The activity was found to be completely absent in the disruption strain (FIG. 2 lane 4). Significantly, the activity could be partially restored by the presence of YNR008w on the single copy plasmid pUS1 (FIG. 2 lane 5). Moreover, acyl groups of phosphatidylethanolamine (PE) were efficiently incorporated into TAG by microsomes from the wild type strain whereas no incorporation occurred from this substrate in the mutant strain. This shows that YNR008w encodes a yeast PDAT which catalyzes the transfer of an acyl group from the sn-2 position of phospholipids to DAG, thus forming TAG. It should be noted that no cholesterol esters were formed from radioactive PC even in incubations with added ergosterols, nor were the amount of radioactive free fatty acids formed from PC affected by disruption of the YNR008w gene. This demonstrates that yeast PDAT do not have cholesterol ester synthesising or phospholipase activities.

Increased TAG content in yeast cells that overexpress PDAT. The effect of overexpressing the PDAT-encoding gene was studied by transforming a wild type yeast strain with the pUS4 plasmid in which the gene is expressed from the galactose-induced GAL1:TPK2 promoter. Cells containing the empty expression vector were used as a control. The cells were grown in synthetic glycerol-ethanol medium, and expression of the gene was induced after either 2 hours (early log phase) or 25 hours (stationary phase) by the addition of galactose. The cells were then incubated for another 21 hours, after which they were harvested and assays were performed. We found that overexpression of PDAT had no significant effect on the growth rate as determined by the optical density. However, the total lipid content, measured as total μmol fatty acids per mg yeast dry weight, was 47% (log phase) or 29% (stationary phase) higher in the PDAT overexpressing strain than in the control. Furthermore, the polar lipid and sterolester content was unaffected by overexpression of PDAT. Instead, the elevated lipid content in these cells is entirely due to an increased TAG content (FIG. 3A,B). Thus, the amount of TAG was increased by 2-fold in PDAT overexpressing early log phase cells and by 40% in stationary phase cells. It is interesting to note that a significant increase in the TAG content was achieved by overexpressing PDAT even under conditions (i.e. in stationary phase) where DAGAT is induced and thus contributes significantly to TAG synthesis. In vitro PDAT activity assayed in microsomes from the PDAT overexpressing strain was 7-fold higher than in the control strain, a finding which is consistent with the increased levels of TAG that we observed in vivo (FIG. 3C). These results clearly demonstrate the potential use of the PDAT gene in increasing the oil content in transgenic organisms.

Substrate specificity of yeast PDAT. The substrate specificity of yeast PDAT was analyzed using microsomes prepared from the PDAT overexpressing strain (see FIG. 4). The rate of TAG synthesis, under conditions given in FIG. 4 with di-oleoyl-PC as the acyl-donor, was 0.15 nmol per min and mg protein. With both oleoyl groups of PC labeled it was possible, under the given assay conditions, to detect the transfer of 11 pmol/min of [$^{14}$C]oleoyl chain into TAG and the formation of 15 pmol/min of lyso-PC. In microsomes from the PDAT-deficient strain, no TAG at all and only trace amounts of lyso-PC was detected, strongly suggesting that yeast PDAT catalyses the formation of equilmolar amounts of TAG and lyso-PC when supplied with PC and DAG as substrates. The fact that somewhat more lyso-PC than TAG is formed can be explained by the presence of a phospholipase in yeast microsomes, which produces lyso-PC and unesterified fatty acids from PC (data not shown).

The specificity of yeast PDAT for different acyl group positions was investigated by incubating the microsomes with di-oleoyl-PC carrying a [$^{14}$C]acyl group either at the sn-1 position (FIG. 4A bar 2) or the sn-2 position (FIG. 4A bar 3). We found that the major $^{14}$C-labeled product formed in the former case was lyso-PC, and in the latter case TAG. We conclude that yeast PDAT has a specificity for the transfer of acyl groups from the sn-2 position of the phospholipid to DAG, thus forming sn-1-lyso-PC and TAG. Under the given assay conditions, trace amounts of $^{14}$C-labelled DAG is formed from the sn-1 labeled PC by the reversible action of a CDP-choline:choline phosphotransferase (data not shown). This labeled DAG can then be further converted into TAG by the PDAT activity. It is therefore not possible to distinguish whether the minor amounts of labeled TAG that is formed in the presence of di-oleoyl-PC carrying a [$^{14}$C]acyl group in the sn-1 position, is synthesized directly from the sn-1-labeled PC by a PDAT that also can act on the sn-1 position, or if it is first converted to sn-1-labeled DAG and then acylated by a PDAT with strict selectivity for the transfer of acyl groups at the sn-2 position of PC. Taken together, this shows that the PDAT encoded by YNR008w catalyses an acyl transfer from the sn-2 position of PC to DAG, thus causing the formation of TAG and lyso-PC.

The substrate specificity of yeast PDAT was further analyzed with respect to the headgroup of the acyl donor, the acyl group transferred and the acyl chains of the acceptor DAG molecule. The two major membrane lipids of S. cerevisiae are PC and PE, and as shown in FIG. 4B (bars 1 and 2), dioleoyl-PE is nearly 4-fold more efficient than dioleoyl-PC as acyl donor in the PDAT-catalyzed reaction. Moreover, the rate of acyl transfer is strongly dependent on the type of acyl group that is transferred. Thus, a ricinoleoyl group at the sn-2 position of PC is 2.5 times more efficiently transferred into TAG than an oleoyl group in the same position (FIG. 4B bars 1 and 3). In contrast, yeast PDAT has no preference for the transfer of vernoloyl groups over oleoyl groups (FIG. 4B bars 1 and 4). The acyl chain of the acceptor DAG molecule also affects the efficiency of the reaction. Thus, DAG with a ricinoleoyl or a vernoloyl group is a more efficient acyl acceptor than dioleoyl-DAG (FIG. 4B bars 1, 5 and 6). Taken together, these results clearly show that the efficiency of the PDAT-catalyzed acyl transfer is strongly dependent on the properties of the substrate lipids.

PDAT genes. Nucleotide and amino acid sequences of several PDAT genes are given as SEQ ID NO. 1 through 15. Further provisional and/or partial sequences are given as SEQ ID NO. 16 through 19, respectively. One of the *Arabidopsis* genomic sequences (SEQ ID NO. 4) identified an *Arabidopsis* EST cDNA clone; T04806. This cDNA clone was fully characterized and the nucleotide sequence is given as SEQ ID NO. 5. Based on the sequence homology of the T04806 cDNA and the *Arabidopsis thaliana* genomic DNA sequence (SEQ ID NO. 4) it is apparent that an additional A is present at position 417 in the cDNA clone (data not shown). Excluding this nucleotide would give the amino acid represented by the nucleotide sequence depicted in SEQ ID NO. 12.

Increased TAG content in seeds of *Arabidopsis thaliana* that express the yeast PDAT. For the expression of the yeast pdat gene in *Arabidopsis thaliana* an EcoRI fragment from the pBluescript-pdat was cloned together with napin promoter (26) into the vector pGPTV-KAN (27). A plasmid (pGNapPDAT) having the yeast PDAT gene in the correct orientation was identified and transformed into *Agrobacterium tumefaciens*. These bacteria were used to transform *Arabidopsis thaliana* columbia (C-24) plants using the root transformation method (28). Plants transformed with an empty vector were used as controls.

First generation seeds (T1) were harvested and germinated on kanamycin containing medium. Second generation seeds (T2) were pooled from individual plants and their fatty acid contents analysed by quantification of their methyl esthers by gas liquid chromatography after methylation of the seeds with 2% sulphuric acid in methanol at 85° C. for 1.5 hours. Quantification was done with heptadecanoic acid methyl esters as internal standard.

From the transformation with pGNapPDAT one T1 plant (26-14) gave raise to seven T2 plants of which 3 plants yielded seeds with statistically (in a mean difference two-sided test) higher oil content than seeds from T2 plants generated from T1 plant 32-4 transformed with an empty vector (table 2).

References cited in the description:
1. Bell, R. M. & Coleman, R. A. (1980) *Ann. Rev. Biochem.* 49, 459-487.
2. Stymne, S. & Stobart, K. (1987) in *The biochemistry of plants: a comprehensive treatsie*, Vol. 9, ed. Stumpf, P. K. (Academic Press, New York), pp. 175-214.
3. Cases, S. et al. (1998) *Proc. Natl. Acad. Sci. U S A* 95, 13018-13023.
4. Hobbs, D. H., Lu, C. & Hills, M. J. (1999) *FEBS Lett.* 452, 145-9
5. Zou, J., Wei, Y., Jako, C., Kumar, A. Selvaraj, G. & Taylor, D. C. (1999) *Plant J.* 19, 645-653.
6. Lardizabal, K., Hawkins, D., Mai, J., & Wagner, N. (1999) Abstract presented at the Biochem. Mol. Plant Fatty Acids Glycerolipids Symposium, South Lake Tahoe, USA.
7. Thomas, B. J. & Rothstein, R. (1989) *Cell* 56, 619-630.
8. Entian, K.-D. & Kötter, P. (1998) *Meth. Microbiol.* 26, 431-449.
9. Kern, L., de Montigny, J., Jund, R. & Lacroute, F. (1990) *Gene* 88, 149-157.
10. Ronne, H., Carlberg, M., Hu, G.-Z. & Nehlin, J. O. (1991) *Mol. Cell. Biol.* 11, 4876-4884.
11. Stobart, K. & Stymne, S. (1990) in *Method in Plant Biochemistry,* vol. 4, eds. Harwood, J. L. & Bowyer, J. R. (Academic press, London), pp. 19-46.
12. Bafor, M., Smith, M. A., Jonsson, L., Stobrt, A. K. & Stymne, S. (1991) *Biochem. J.* 280, 507-514.
13. Banas, A., Johansson, I. & Stymne, S. (1992) *Plant Science* 84, 137-144.
14. Kanda, P. & Wells, M. A. (1981) *J. Lipid. Res.* 22, 877-879.
15. Ståhl, U., Ek, B. & Stymne, S. (1998) *Plant Physiol.* 117, 197-205.
16. Stobart, K., Mancha, M. & Lenman M. Dahlqvist, A. & Stymne, S. (1997) *Planta* 203, 58-66.
17. Bligh, E. G. & Dyer, W. J. (1959) *Can. J. Biochem. Physiol.* 37, 911-917.
18. Sherman, F., Fink, G. R. & Hicks, J. B. (1986) in *Laboratory Course Manual for Methods in Yeast Genetics* (Cold Spring Harbor Laboratory).
19. Meesters, P. A. E. P., Huijberts, G. N. M. and Eggink, G. (1996) *Appl. Microbiol. Biotechnol.* 45, 575-579.
20. van de Loo, F. J., Fox, B. G. & Sommerville, C. (1993), in *Lipid metabolism in plants,* ed. Moore, T. S. (CRC Press, Inc.), pp. 91-126.
21. van de Loo, F. J., Broun, P., Turner, S. & Sommerville, S. (1995) *Proc. Natl. Acad. Sci. U S A* 95, 6743-6747.
22. Lee, M., Lenman, M., Banas, A., Bafor, M., Singh, S., Schweizer, M., Nilsson, R., Liljenberg, C., Dahlqvist, A., Gummeson, P-O., Sjödahl, S., Green, A., and Stymne, S. (1998) *Science* 280, 915-918.
23. Glomset, J. A. (1968) *J. Lipid Res.* 9, 155-167.
24. Thompson, J. D., Gibson, T. J., Plewniak, F., Jeanmougin, F. & Higgins, D. G. (1997) *Nucl. Acids Res.* 24, 4876-4882.
25. Saitou, N. & Nei, M. (1987) *Mol. Biol. Evol.* 4, 406-425.
26. Stålberg, K., Ellerström, M., Josefsson, L., & Rask, L. (1993) *Plant Mol. Biol.* 23, 671.
27. Becker, D., Kemper, E., Schell, J., Masterson, R. (1992) *Plant Mol. Biol.* 20, 1195.
28. D. Valvekens, M. Van Montagu, and Van Lusbettens (1998) Proc. Natl. Acad. Sci. U.S.A. 85, 5536.

The invention claimed is:

1. A process for the production of triacylglycerol, comprising: growing a transgenic plant cell or a yeast cell, a fungi, or a plant containing
   (i) the nucleotide sequence of SEQ ID NO: 1 from *Saccharomyces cerevisiae*, or
   (ii) the nucleotide sequence that is 95% identical to said SEQ ID NO:1, wherein the nucleotide sequence of (i) and (ii) encode an enzyme (SEQ ID NO:2) that catalyzes in an acyl-CoA-independent reaction the transfer of fatty acids from phospholipids to diacylglycerol in the biosynthetic pathway for the production of triacylglycerol.

2. A method of producing triacylglycerol or triacylglycerols with uncommon fatty acids comprising:
   transforming a plant cell or a yeast cell, a fungi, or a plant which produces uncommon fatty acids with
   (i) the nucleotide sequence of SEQ ID NO: 1 from *Saccharomyces cerevisiae*, or
   (ii) the nucleotide sequence that is 95% identical to said SEQ ID NO: 1, wherein
   the nucleotide sequence of (i) and (ii) encode SEQ ID NO: 2 whereby transformation results in the production of an enzyme (SEQ ID NO: 2) that catalyzes in an acyl-CoA-independent reaction the transfer of fatty acids from phospholipids to diacylglycerol in the biosynthesis pathway for the production of triacylglycerol or triacylglycerols with uncommon fatty acids.

3. A method of producing triacylglycerol or triacylglycerols for increasing the oil content of an organism or cell comprising:
   transfecting a plant cell or a yeast cell, a fungi, or a plant with
   (i) the nucleotide of sequence of SEQ ID NO: 1 from *Saccharomyces cerevisiae*, or
   (ii) the nucleotide sequence 95% identical to said SEQ ID NO: 1,
   wherein the nucleotide sequence of (i) and (ii) encodes SEQ ID NO: 2 whereby transfection results in the production of an enzyme (SEQ ID NO: 2) that catalyzes in an acyl-CoA-independent reaction the transfer of fatty acids from phospholipids to diacylglycerol in the biosynthesis pathway for the production of triacylglycerol or triacylglycerols thereby increasing the oil content of the plant cell or the yeast cell, the fungi, or the plant.

4. The method of claim 3 wherein the oil content is increased in seeds.

5. The process of claim 1 wherein the process comprises the step of growing a transgenic plant or yeast cell, or plant.

6. The method of claim 2 wherein the method comprises the step of transforming a transgenic plant or yeast cell, or plant.

7. The method of claim 3 wherein the method comprises the step of transfecting a transgenic plant or yeast cell, or plant.

8. The method of claim 2 wherein the uncommon fatty acids are in the form of phospholipids.

\* \* \* \* \*

UNITED STATES PATENT AND TRADEMARK OFFICE
CERTIFICATE OF CORRECTION

PATENT NO. : 7,427,593 B2 Page 1 of 1
APPLICATION NO. : 09/537710
DATED : September 23, 2008
INVENTOR(S) : Dahlqvist et al.

It is certified that error appears in the above-identified patent and that said Letters Patent is hereby corrected as shown below:

Title Pg, Item (57)
Line 5 of the Abstract:
"in any acyl–CoA–independent" should read -- in an acyl–CoA–independent --

In Claim 2, col. 60, indicated lines 46–47:
"biosynthesis pathway" should read -- biosynthetic pathway --

In Claim 3, col. 60, indicated lines 64–65:
"biosynthesis pathway" should read -- biosynthetic pathway --

Signed and Sealed this

Tenth Day of March, 2009

JOHN DOLL
*Acting Director of the United States Patent and Trademark Office*